United States Patent
Yu et al.

(10) Patent No.: US 9,925,202 B2
(45) Date of Patent: Mar. 27, 2018

(54) TREATMENT OF LYMPHANGIOLEIOMYOMATOSIS

(71) Applicant: THE BRIGHAM AND WOMEN'S HOSPITAL, INC., Boston, MA (US)

(72) Inventors: Jane Yu, Cincinnati, OH (US); Chenggang Li, Maineville, OH (US)

(73) Assignee: BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/771,817

(22) PCT Filed: Mar. 4, 2014

(86) PCT No.: PCT/US2014/020125
§ 371 (c)(1),
(2) Date: Sep. 1, 2015

(87) PCT Pub. No.: WO2014/137978
PCT Pub. Date: Sep. 12, 2014

(65) Prior Publication Data
US 2016/0022706 A1    Jan. 28, 2016

Related U.S. Application Data

(60) Provisional application No. 61/851,249, filed on Mar. 4, 2013.

(51) Int. Cl.
| *A61K 31/616* | (2006.01) |
| *A61K 31/192* | (2006.01) |
| *A61K 31/436* | (2006.01) |
| *A61K 31/18* | (2006.01) |
| *A61K 45/06* | (2006.01) |
| *A61K 31/12* | (2006.01) |
| *A61K 31/196* | (2006.01) |
| *A61K 31/365* | (2006.01) |
| *A61K 31/405* | (2006.01) |
| *A61K 31/415* | (2006.01) |
| *A61K 31/42* | (2006.01) |

(52) U.S. Cl.
CPC ............ *A61K 31/616* (2013.01); *A61K 31/12* (2013.01); *A61K 31/18* (2013.01); *A61K 31/192* (2013.01); *A61K 31/196* (2013.01); *A61K 31/365* (2013.01); *A61K 31/405* (2013.01); *A61K 31/415* (2013.01); *A61K 31/42* (2013.01); *A61K 31/436* (2013.01); *A61K 45/06* (2013.01)

(58) Field of Classification Search
CPC ...... A61K 31/616; A61K 31/18; A61K 45/06; A61K 31/436; A61K 31/192
USPC .... 514/35, 161, 163, 171, 254.06, 275, 291, 514/600, 77
See application file for complete search history.

(56) References Cited

U.S. PATENT DOCUMENTS

| 5,972,988 A | 10/1999 | Macias |
| 6,426,351 B1 | 7/2002 | Weichselbaum et al. |
| 7,811,776 B2 | 10/2010 | McCormack et al. |
| 2005/0266442 A1 | 12/2005 | Squillance et al. |
| 2009/0325876 A1 | 12/2009 | Yedgar et al. |
| 2010/0298352 A1 | 11/2010 | Prochownik et al. |
| 2010/0305150 A1 | 12/2010 | Berg |
| 2012/0128670 A1 | 5/2012 | Barr |
| 2012/0196870 A1 | 8/2012 | Arbiser |
| 2012/0213778 A1 | 8/2012 | Rastelli et al. |
| 2012/0264784 A1 | 10/2012 | Bear et al. |

FOREIGN PATENT DOCUMENTS

| WO | 2004/080445 A1 | 9/2004 |
| WO | 2009/045443 A2 | 4/2009 |
| WO | 2011/123524 A2 | 10/2011 |

OTHER PUBLICATIONS

Inoue et al. Lipophilic HMG-CoA reductase inhibitor has an anti-inβammatory effect Reduction of MRNA levels for interleukin-1b, interleukin-6, cyclooxygenase-2, and p22phox by regulation of peroxisome proliferator-activated receptor a (PPAR a) in primary endothelial cells. Life Sciences 67 (2000) 863-876.*
Hirota et al. Heightened uterine mammalian target of rapamycin complex 1 (mTORC1) signaling provokes preterm birth in mice. PNAS | Nov. 1, 2011 | vol. 108 | No. 44 | 18073-18078.*
Vane et al. New insights into the mode of action of anti-inflammatory drugs. Inflamm Res 44:1-10 (1995).*
Li et al. Estradiol and mTORC2 cooperate to enhance prostaglandin biosynthesis and tumorigenesis in TSC2-deficient LAM cells. J. Exp. Med. Jan. 2014 vol. 211 No. 1 p. 15-28, accepted on Dec. 9, 2013. (Year: 2013).*
Garcia-Garcia et al., "Phospholipase A2 inhibitors", Curr Opin Lipidol, 20(4):327-32 (2009).
Aissat et al., "Antiproliferative effects of rapamycin as a single agent and in combination with carboplatin and paclitaxel in head and neck cancer cell lines", Cancer Chemother Pharmacol, 62(2):305-13 (2008).
Chmura et al., "Decreasing the apoptotic threshold of tumor cells through protein kinase C inhibition and sphingomyelinase activation increases tumor killing by ionizing radiation", Cancer Res, 57(19):4340-7 (1997).

(Continued)

*Primary Examiner* — Shaojia A Jiang
*Assistant Examiner* — Yih-Horng Shiao
(74) *Attorney, Agent, or Firm* — Nixon Peabody LLP; David S. Resnick

(57) ABSTRACT

Embodiments disclosed herein provide compositions and methods for treating lymphangioleiomyomatosis (LAM) comprising inhibiting COX overexpression and prostaglandin over production by administering at least one COX inhibitor and/or prostaglandin biosynthetic pathway inhibitors. Lymphangioleiomyomatosis (LAM) is a rare lung disease. Some LAM occurances are associated with mutations in the tuberous sclerosis complex (TSC) locus. LAM occurs almost exclusively in women, usually of childbearing age.

15 Claims, 17 Drawing Sheets

(56) References Cited

OTHER PUBLICATIONS

Chmura et al., "In vitro and in vivo activity of protein kinase C inhibitor chelerythrine chloride induces tumor cell toxicity and growth delay in vivo", Clin Cancer Res, 6(2):737-42 (2000).
Gao et al., "Effects of a protein kinase C inhibitor combined with cisplatin on non-small cell lung cancer" Zhonghua Jie He He Hu Xi Za Zhi, 33(4):284-8 [Abstract] (2010).
Klein et al., "A switch in RND3-RHOA signaling is critical for melanoma cell invasion following mutant-BRAF inhibition," Klein and Higgens, Molecular Cancer, 10:114 (2011).
Riley et al., "Darapladib, a reversible lipoprotein-associated phospholipase A2 inhibitor, for the oral treatment of atherosclerosis and coronary artery disease", Idrugs, 12(10):648-655 (2009).
Cohen et al., Clin Cancer Res., 15(21):6694-6701 (2009). "A Phase I Dose-Escalation Study of Danusertib (PHA-739358) Administered as a 24-hour Infusion With and Without G-CSF in a 14-day Cycle in Patients with Advanced Solid Tumors."
Glasgow et al., Respir Med., 104(Suppl 1):S45-S58 (2010). "Lymphagioleiomyomatosis (LAM): Molecular insighs to lead to targeted therapies."
Guertin et al., Trends Mol Med. Aug. 2005;11(8):353-61. "An expanding role for mTOR in cancer."
Ikezoe et al., International Journal of Cancer, 129(10):2512-2521 (2011). "Expression of p-JAK2 predicts clinical outcome and is a potential molecular target of acute myelogenous leukemia."
Johnson et al., Eur. Respi J., 35(1):14-26, (2010). European Respiratory Society guidelines for the diagnosis and management of lymphagioleiomyomatosis.
Johnson, S.R. Respiratory Medicine. 1041(1):s33-s41 (2010). "The ERS guidelines for LAM: trying a rationale approach to a rare disease."
Kenerson et al, Pediatric Research, 57(1):67-75. "Effects of Rapamycin in the Eker Rat Model fo Tuberous Sclerosis Complex.", (2005).
Klein et al., Kleinand Higgens, Molecular Cancer, 10:114 (2011). "A switch in RND3-RHOA signaling is critical for melanoma cell invasion following mutant-BRAF inhibition."
Laplante et al., Cell. Apr. 13, 2012;149(2):274-93. "mTOR signaling in growth control and disease."
Li et al. Journal of Experimental Medicine, 211(1):15-28 (2014). "Estradiol and mTORC2 cooperate to enhance prostaglandin biosynthesis and tumorigenesis in TSC2-deficient LAM cells".
Okamoto et al., Cancer Science, 94(1):22-25 (2003). "Down-regulation of cyclooxygenase-2 expression but up-regulation of cyclooxygenase-1 in renal carcinomas of the Eker (TSC2 gene mutant) rat model."
Parekh et al., Journal fo Physiology, 489.2:377-382 (1995). "Activation of store-operated calcium influx at resting InsP3 levels by sensitization of the InsP3 receptor in rat basophilic leukaemia cells."
Prokazona et al., Biochemistry, 63(1):31-37, (1998). "Effect of lysophosphatidylcholine on transmembrane signal transduction".
Rankin et al., Br. J. Cancer, 65:275-281 (1992). "A randomised study comparing standard dose carboplatin with chlorambucil and carboplatin in advanced ovarian cancer."
Riley et al., Idrugs, 12(10):648-655, (2009). "Darapladid a reversible lipoprotein-associated phospholipase A2 inhibitor, for the oral treatment of atherosclerosis and coronary artery disease".
Tee et al., "Tuberous sclerosis complex-1 and -2 gene products function together to inhibit mammalian target of rapamycin (mTOR)-mediated downstairs signaling", PNAS, 99(21):13571-13576 (2002).
Tee et al., Seminars in Cell & Development Biology, 16:29-37 (2005). "mtor, translational control and human disease".
Wong, M., "Mammalian target rapamycin (mTOR) inhibition as a potential antiepileptogenic therapy: From tuberous sclerosis to common acquired epilepsis", Epilepsia 51(1):27-36 (2010).
Yuan e tal., Journal of Hematology & Oncology, 2:45 (2009). "Targeting tumorigenesis: development and use of mTOR inhibitors in cancer therapy."

* cited by examiner

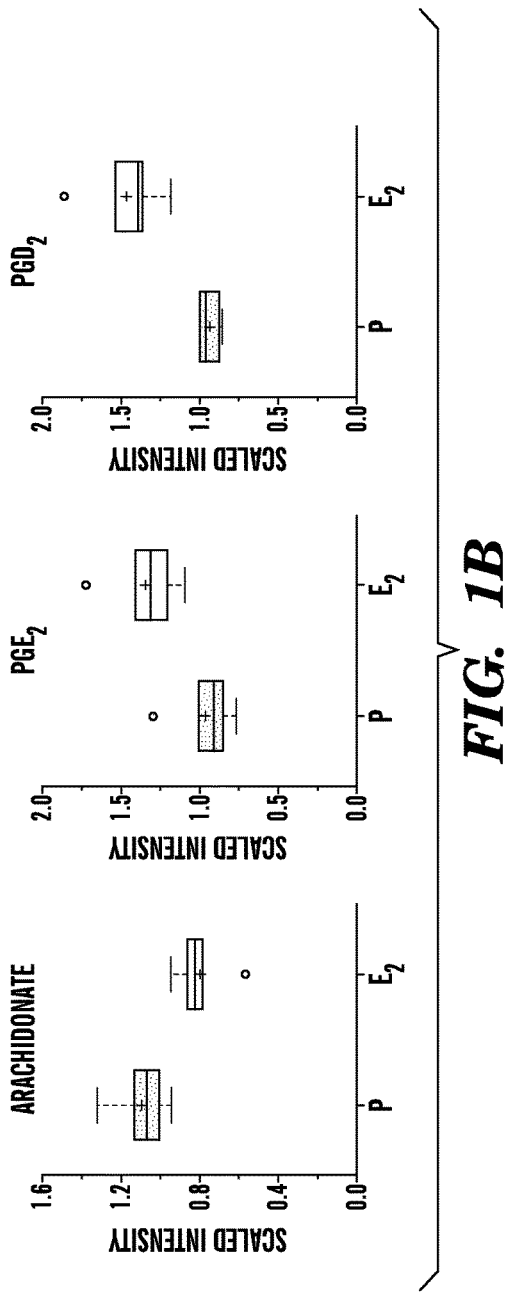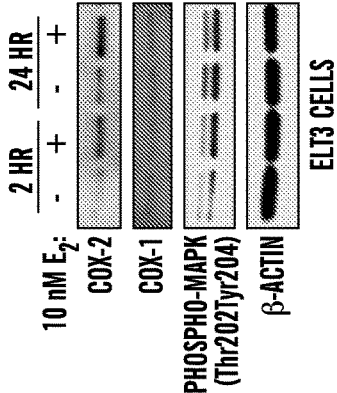
FIG. 1B
FIG. 1C
FIG. 1D

ELT3 CELLS

*Tsc2$^{+/-}$* RENAL TUMOR

Figure 6

| Gene | Protein | TSC2-<br>vs<br>TSC2+ | Rapa TSC2-<br>vs<br>Veh TSC2- |
|---|---|---|---|
| *PTGS2*<br>*(COX-2)* | Prostaglandin endoperoxide<br>synthase 2 | 2.1<br>($p$ = 0.004) | 1.3<br>($p$ = 0.05) |
| *PTGIS* | Prostaglandin I2<br>(prostacyclin) synthase | 40.4<br>($p$ = 0.00001) | 1.5<br>($p$ = 0.0006) |

**Rapamycin-Insensitive Up-Regulation of *MMP2* and Other Genes in
Tuberous Sclerosis Complex 2–Deficient LAM-Like Cells**
Lee... Kwiatkowski 2010 (Am J Resp Cel Mol Biol)

TREATMENT OF LYMPHANGIOLEIOMYOMATOSIS

CROSS REFERENCE TO RELATED APPLICATION

This application is a 35 U.S.C. § 371 National Phase Entry Application of International Application No.: PCT/US2014/020125 filed Mar. 4, 2014, which designates the U.S., and which claims benefit under 35 U.S.C. § 119(e) of the U.S. provisional application No. 61/851,249 filed Mar. 4, 2013, the contents of each of which are incorporated herein by reference in their entirety.

GOVERNMENT SUPPORT

This invention was made with Government support under Grant No.: RO1 HL098216-3 awarded by the National Institutes of Health, and Grant No.: W8IXBH-12-1 awarded by the Department of Defense. The Government has certain rights in the invention.

TECHNICAL FIELD

The disclosure herein relates to compositions and methods for the treatment of lymphangioleiomyomatosis (LAM) and lymphangioleiomyomatosis in tuberous sclerosis complex (TSC/LAM).

BACKGROUND

Lymphangioleiomyomatosis (LAM) is a rare lung disease. Some LAM occurances are associated with mutations in the tuberous sclerosis complex (TSC) locus. LAM occurs almost exclusively in women, usually of childbearing age. There are two types of LAM, sporadic LAM and LAM/TSC which is LAM that frequently occurs in patients who have TSC.

LAM is characterized by the proliferation of abnormal smooth muscle-like cells throughout the lungs, in the bronchioles, alveolar septa, perivascular spaces, and lymphatics, resulting in the obstruction of small airways that leads to pulmonary cyst formation and pneumothorax, and lymphatics that leads to chylous pleural effusion.

TSC is a rare multi-system genetic disease that results in the growth of nonmalignant tumors in the brain and on other vital organs such as the kidneys, heart, eyes, lungs, brain, and skin. A combination of symptoms may include seizures, developmental delay, behavioral problems, skin abnormalities, and lung and kidney disease. TSC is caused by a mutation of either of two genes, TSC1 and TSC2, with the TSC2 mutation being the more typical TSC mutation. The mutations in the TSC locus tend to be negative mutations that lead to no or reduced amount of functional TSC 1 or 2 gene product. This in turn leads to a deregulation of the mTOR signaling pathway.

The mammalian target of rapamycin (mTOR) signaling pathway is a major player controlling cell growth and cell division. The kinase, mTOR, is a master regulator of protein synthesis that couples nutrient sensing to cell growth. Defects in the mTOR signaling pathway can result in loss of control in cell growth and cell division. For example, two proteins, hamartin and tuberin, are known to be involved in the control of cell growth and cell division via their effects on the mTOR signaling pathway. Hamartin and tuberin function as a complex to interact with Rheb GTPase, thereby sequestering it from activating mTOR signaling. Mutations at the TSC1 and TSC2 loci which codes for hamartin and tuberin respectively result in the deregulation of the mTOR signaling pathway resulting in increased mTOR signaling. This in turn leads to a loss of control of cell growth and cell division, and subsequently a predisposition to forming tumors.

High percentages (60-80%) of TSC patients have benign tumors in the kidneys called angiomyolipomas (AML) which frequently causing hematuria. These tumors are composed of vascular tissue (angio-), smooth muscle (-myo-), and fat (-lipoma). Although benign, AML may grow such that kidney function is impaired or the blood vessels may dilate and burst leading to catastrophic hemorrhage either spontaneously or with minimal trauma. Large AML can be treated with embolization.

In addition, TSC patients who have AML are predisposed to develop LAM in the lungs. The proliferating smooth muscle that occurs in the type of LAM seen in these patients (TSC-LAM) has been shown to represent clones of the smooth muscle in those patients' renal AML. It is believed to represent metastases of this "benign" tumor.

Leading causes of death in TSC patients include renal disease, brain tumor, LAM of the lung, and status epilepticus or bronchopneumonia in those with severe mental handicap. There is no current effective treatment for TSC or the consequential AML or LAM; treatment is mainly symptomatic management, e.g., everolimus (derivative of rapamycin) for the treatment of subependymal giant cell astrocytoma (brain tumor), vigabatrin for infantile spasm, ACTH for epilepsy and rapamycin for shrinking the tumors.

The clinical course of patients with LAM shows considerable variation. The disease can progress slowly, but ultimately leads to respiratory failure and death. The 10-year survival rate from the start of symptoms has been reported to range from 47-79% depending on the various studies. Current treatments include administration of rapamycin (also known as sirolimus, an mTOR inhibitor) for shrinking tumors, and therapies targeting the reproductive cycle of the women, e.g., progesterone, oophorectomy, tamoxifen, gonadotropin-releasing hormone (GnRH) agonists or analogues and androgen therapy. Although the mTORC1 inhibitor rapamycin has been shown to stabilize lung function and improved symptoms in these patients, the lung function tend to declined when rapamycin was discontinued. Improvement to the current repertoire of therapies for LAM and LAM/TSC are needed.

SUMMARY

The methods and compositions provided herein relate, in part, to the discovery of cancer cells and tumors of lymphangioleiomyomatosis (LAM) are responsive to aspirin; they decreased in size and reduced proliferation when treated with aspirin. The inventors observed that the expression of cyclooxygenase-2 (COX-2) and prostaglandin production are elevated in a rapamycin-insensitive and Torin1-sensitive manner in TSC2-deficient cells, but not in TSC2-reexrpessing cells.

Accordingly, inhibitors of a COX or the prostaglandin biosynthetic pathway are useful for inhibiting the cell proliferation of cancer cells and tumors of LAM and therefore for treating LAM.

Accordingly, it is the objective of this disclosure to provide additional therapeutics to the existing repertoire of therapies currently available for LAM. Compositions and methods are provided for treating lymphangioleiomyomatosis (LAM) comprising inhibiting COX overexpression and prostaglandin over production by administering at least one COX inhibitor and/or prostaglandin biosynthetic pathway inhibitors.

Accordingly, in one embodiment, provided herein is a method for treating LAM in a subject in need comprising administering to a subject therapeutically effective amount of a cyclooxygenase (COX) inhibitor or an inhibitor of the prostaglandin biosynthetic pathway.

In one embodiment, provided herein is a method for treating LAM in a subject in need comprising selecting a subject having LAM and administering to the subject therapeutically effective amount of a COX inhibitor or an inhibitor of the prostaglandin biosynthetic pathway.

In one embodiment, provided herein is a method for treating LAM in a subject in need comprising selecting a subject having LAM and has a mutation in the TSC locus, and administering to the subject therapeutically effective amount of a COX inhibitor or an inhibitor of the prostaglandin biosynthetic pathway.

In one embodiment, provided herein is a method for treating LAM in a subject in need comprising selecting a subject having cancer cells that are TSC-1 or TSC-2 deficient or both TSC1/2 deficient and administering to the subject therapeutically effective amount of a COX inhibitor or an inhibitor of the prostaglandin biosynthetic pathway.

In one embodiment, provided herein is a method for treating LAM in a subject in need comprising selecting a subject having COX overexpression and administering to the subject therapeutically effective amount of a COX inhibitor or an inhibitor of the prostaglandin biosynthetic pathway.

In one embodiment, provided herein is a method for treating LAM in a subject in need comprising selecting a subject having increased prostaglandin production and administering to the subject therapeutically effective amount of a COX inhibitor or an inhibitor of the prostaglandin biosynthetic pathway.

In one embodiment, provided herein is a method for treating LAM in a subject in need comprising selecting a subject having a mutation in the TSC locus and having a COX overexpression and/or increased prostaglandin production, and administering to the subject therapeutically effective amount of a COX inhibitor or an inhibitor of the prostaglandin biosynthetic pathway.

In one embodiment, provided herein is a method for treating LAM in a subject in need comprising selecting a subject having LAM and having a COX overexpression and/or increased prostaglandin production, and administering to the subject therapeutically effective amount of a COX inhibitor or an inhibitor of the prostaglandin biosynthetic pathway.

In one embodiment, provided herein is a method for treating LAM in a subject in need comprising selecting a subject having a mutation in the TSC locus and having increased prostaglandin production, and administering to the subject therapeutically effective amount of a COX inhibitor or an inhibitor of the prostaglandin biosynthetic pathway.

In one embodiment, provided herein is a method for treating LAM in a subject in need comprising selecting a subject having LAM and having increased prostaglandin production and administering to the subject therapeutically effective amount of a COX inhibitor or an inhibitor of the prostaglandin biosynthetic pathway.

In one embodiment, provided herein is a method for treating LAM in a subject in need comprising and having selecting a subject having a mutation in the TSC locus and having a COX overexpression, and administering to the subject therapeutically effective amount of a COXinhibitor or an inhibitor of the prostaglandin biosynthetic pathway.

In one embodiment, provided herein is a method for treating LAM in a subject in need comprising and having selecting a subject having having LAM and having a COX overexpression, and administering to the subject therapeutically effective amount of a COXinhibitor or an inhibitor of the prostaglandin biosynthetic pathway.

In one embodiment, provided herein is a method for treating LAM in a subject in need comprising first determining whether the subject has one or more of the following: (a) a COX overexpression; (b) a mutation in the TSC locus; (c) increased prostaglandin production; (d) mTOR deregulation or hyperactivity ie., normal mTOR regulation or activity; and (e) at least one cancer cell that is insensitive to rapamycin; and if any is affirmative or positive, administering to the subject therapeutically effective amount of a COXinhibitor or an inhibitor of the prostaglandin biosynthetic pathway.

In one embodiment of any method described, the method further comprises determining whether the subject has a negative mutation in the TSC gene 1 or 2.

In one embodiment of any method described, the method further comprises selecting the subject having a mutation in the TSC locus.

In one embodiment of any method described, the method further comprises determining whether the cancer cells of the subject are TSC-1 or TSC-2 or both TSC-1 and TSC-2 deficient.

In one embodiment of any method described, the method further comprises selecting the subject having cancer cells that are TSC-1 or TSC-2 or both TSC-1 and TSC-2 deficient.

In one embodiment of any method described, the method further comprises selecting the subject having a COX overexpression.

In one embodiment of any method described, the method further comprises selecting the subject having increased prostaglandin production.

In one embodiment of any method described, the subject has a mutation in the TSC locus, for example, in the TSC1 or TSC2 or both TSCs.

In one embodiment of any method described, the mutation is a negative mutation that produces loss-of-function of the affected gene. This in essense leads to cells that are deficient in TSC-1 or TSC-2 or both proteins.

In one embodiment of any method described, the cancer cells of the subject are TSC-1 or TSC-2 deficient.

In one embodiment of any method described, the subject has a COX overexpression. In one embodiment of any method described, the COX overexpression is COX-1 or COX-2 or both.

In one embodiment of any method described, the subject has increased prostaglandin production.

In one embodiment of any method described, at least one cancer cell of the subject is insensitive to rapamycin.

In one embodiment of any method described, at least one cancer cell of the subject does not involve mTOR deregulation or hyperactivity. This means that there is normal mTOR regulation or activity in the cancer cell comparable to normal control cells.

In one embodiment of any method described, the subject is further treated with an effective amount of one or more compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, and A-77636.

In one embodiment of any method described, the subject is further treated with a therapeutically effective amount of rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil.

In one embodiment of any method described, the subject is further treated with at least one additional therapy.

In one embodiment of any method described, the at least one additional therapy is a cancer therapy.

In one embodiment of any method described, the at least one additional cancer therapy is selected from the group consisting of radiation therapy, chemotherapy, immunotherapy and gene therapy.

In one embodiment of any method described, the additional cancer therapeutics are known drugs that are not currently being use for the treatment of cancer, LAM, or TSC.

In one embodiment of any method described, subject is further treated with hormone therapy such as progesterone, oophorectomy, tamoxifen, gonadotropin-releasing hormone (GnRH) agonists or analogues and androgen therapy.

In one embodiment of any method described, the subject is human.

In one embodiment of any method described, the therapeutically effective amount of the inhibitor is administered by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and parenteral administration.

In one embodiment of any method described, the COX inhibitor is a COX-1 or COX-2 inhibitor.

In one embodiment of any method described, the COX inhibitor is a selective COX-1 or a selective COX-2 inhibitor.

In one embodiment of any method described, the COX inhibitor is selected from the group of rofecoxib, celecoxib, valdecoxib, nimesulide, ibuprofen, diclofenac, nabumetone, naprosen, aspirin and analogs thereof.

In one embodiment of any method described, the inhibitor of the prostaglandin biosynthetic pathway is indomethacin and flufenamic acid.

In one embodiment of any method described herein, a tumor in the subject being treated is reduced in size by at least 5%.

In one embodiment of any method described herein, the subject being treated has a reduction in prostaglandin production by at least 5%.

In one embodiment of any method described herein, the subject being treated has a reduction in COX overexpression by at least 5%.

In one embodiment of any method described herein, the subject being treated has an improvement of lung function by at least 5%.

In one embodiment, provided herein is a composition comprising at least one a cyclooxygenase (COX) inhibitor and/or an inhibitor of the prostaglandin biosynthetic pathway for the treatment of lymphangioleiomyomatosis (LAM).

In one embodiment, provided herein is a composition comprising at least one a cyclooxygenase (COX) inhibitor and/or an inhibitor of the prostaglandin biosynthetic pathway and rapamycin for the treatment of lymphangioleiomyomatosis (LAM).

In one embodiment, provided herein is a composition comprising at least one a COX inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a composition comprising at least one a COX inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment of any composition described, the composition further comprises at least one pharmaceutically acceptable carrier.

In one embodiment, provided herein is a use of at least one a COX inhibitor and/or an inhibitor of the prostaglandin biosynthetic pathway for the treatment of LAM.

In one embodiment, provided herein is a use of at least one a COX inhibitor and/or an inhibitor of the prostaglandin biosynthetic pathway for the manufacture of medicament for treatment of LAM.

In one embodiment, provided herein is a combinatorial use of at least one a COX inhibitor and/or an inhibitor of the prostaglandin biosynthetic pathway and rapamycin for the treatment of LAM.

In one embodiment, provided herein is a combinatorial use of at least one a COX inhibitor and/or an inhibitor of the prostaglandin biosynthetic pathway and rapamycin for the manufacture of medicament for treatment of LAM.

In one embodiment, provided herein is a combinatorial use of at least one a COX inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a combinatorial use of at least one a COX inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the manufacture of medicament for the treatment of LAM.

In one embodiment, provided herein is a combinatorial use of at least one a COX inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a combinatorial use of at least one a COX inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the manufacture of medicament for the treatment of LAM.

In one embodiment, provided herein is a method for inhibiting cell growth, the method comprising contacting a cell with an effective amount of a COX inhibitor or an inhibitor of the prostaglandin biosynthetic pathway. In some embodiments, the inhibition of cell growth is measured in terms of apoptosis or cell proliferation.

In one embodiment of any method described herein, each inhibitor or additional compound is administered singly, i.e., each each inhibitor or additional compound is administered independently of the others. In another embodiment of any method described, the each inhibitor or additional compounds are administered singly and simultaneously. In another embodiment, the each inhibitor or compounds are administered together, e.g., in a cocktail or admixture.

In one embodiment of any method or composition described, the inhibitor is singly administered by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and parenteral routes of administration. In one embodiment, where more than one inhibitor or compound is used for treatment, the inhibitor and/or compounds are administered simultaneously. In another embodiment, where more than one inhibitor or compound is used for treatment, the inhibitor and/or compounds are administered sequentially. The inhibitor and/or compounds can be admixed prior to administration and administered together, for example, in a single pharmaceutical composition.

In some embodiments, the one or more inhibitor and/or additional compound used for treatment is administering by nasal inhalation such as via a nebulizer. For example, the inhibitor and/or additional compound is formulated as a powder for delivery via a nebulizer.

In one embodiment of any composition described, the composition comprising at least one inhibitor and/or compound is administered singly or in combination by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and and parenteral administration.

In one embodiment of any composition described, the composition is formulated for administration by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and, and parenteral administration.

In one embodiment of any of the methods or compositions described herein, derivatives or analogues of the known drugs/compounds are included.

In one embodiment, provided herein is a method for treating LAM in a subject in need comprising (a) determining whether the subject has a mutation in the tuberous sclerosis TSC locus and (b) administering to the subject therapeutically effective amount of any composition described herein when the subject is determined to have a TSC mutation.

In one embodiment, provided herein is a method for treating LAM in a subject in need comprising (a) selecting a subject having COX-1 or COX-2 overexpression; and (b) administering to the subject therapeutically effective amount of any composition described herein.

In one embodiment, provided herein is a method for treating LAM in a subject in need comprising (a) selecting a subject having increased prostaglandin production; and (b) administering to a subject therapeutically effective amount of any composition described herein.

In one embodiment, provided herein is a method for treating LAM in a subject in need comprising (a) selecting the subject having a negative mutation in the TSC locus and (b) administering to a subject therapeutically effective amount of any composition described herein.

In one embodiment, provided herein is a method for treating LAM in a subject in need comprising (a) selecting a subject who has at least one cancer cell that is insensitive to rapamycin; and (b) administering to a subject therapeutically effective amount of any composition described herein.

In one embodiment, provided herein is a method for treating LAM in a subject in need comprising (a) selecting a subject who has at least one cancer cell that does not have mTOR deregulation or hyperactivity; and (b) administering to a subject therapeutically effective amount of any composition described herein.

In one embodiment, provided herein is a method for treating LAM in a subject in need comprising (a) selecting a subject having LAM and (b) administering to the subject therapeutically effective amount of any composition described herein.

In one embodiment, provided herein is a method for treating LAM in a subject in need comprising selecting a subject having LAM and has a mutation in the TSC locus, and administering to the subject therapeutically effective amount of any composition described herein.

In one embodiment, provided herein is a method for treating LAM in a subject in need comprising selecting a subject having a mutation in the TSC locus and having a COX overexpression and/or increased prostaglandin production, and administering to the subject therapeutically effective amount of any composition described herein.

In one embodiment, provided herein is a method for treating LAM in a subject in need comprising selecting a subject having LAM and having a COX overexpression and/or increased prostaglandin production, and administering to the subject therapeutically effective amount of any composition described herein.

In one embodiment, provided herein is a method for treating LAM in a subject in need comprising selecting a subject having a mutation in the TSC locus and having increased prostaglandin production, and administering to the subject therapeutically effective amount of any composition described herein.

In one embodiment, provided herein is a method for treating LAM in a subject in need comprising selecting a subject having LAM and having increased prostaglandin production and administering to the subject therapeutically effective amount of any composition described herein.

In one embodiment, provided herein is a method for treating LAM in a subject in need comprising and having selecting a subject having a mutation in the TSC locus and having a COX overexpression, and administering to the subject therapeutically effective amount of any composition described herein.

In one embodiment, provided herein is a method for treating LAM in a subject in need comprising and having selecting a subject having having LAM and having a COX overexpression, and administering to the subject therapeutically effective amount of any composition described herein.

In one embodiment, provided herein is a method for treating LAM in a subject in need comprising first determining whether the subject has one or more of the following: (a) a COX overexpression; (b) a mutation in the TSC locus; (c) increased prostaglandin production; (d) mTOR deregulation or hyperactivity ie., normal mTOR regulation or activity; and (e) at least one cancer cell that is insensitive to rapamycin; and if any is affirmative or positive, administering to the subject therapeutically effective amount of any composition described herein. In some embodiments, the cancer cells also have lower levels of phospho-Akt S473, higher levels of phospho-MARK or phospho-S6 S235.

In one embodiment, provided herein is a method for treating LAM in a subject in need comprising first determining whether the cancer cells of the subject has one or more of the following features:(a) a mutation in the TSC locus; (b) are TSC-1 or TSC-2 deficient; (c) have overexpression of COX-1 or COX-2; (d) have lower levels of phosphos-Akt S473; (d) have higher levels of phosphos-MAPK; (e) have higher levels of phospho-S6 S235; (f) have increased production of prostaglandin; (g) insensitive to rapamycin; and (h) do do not have mTOR deregulation or hyperactivity; and if any is affirmative or positive, administering to the subject therapeutically effective amount of any composition or at least one COX inhibitor and/or an inhibitor of the prostaglandin biosynthesis pathway or described herein.

In one embodiment, provided herein is a method for treating LAM in a subject in need comprising selecting a subject who has the cancer cells that have one or more of the following features:(a) a mutation in the TSC locus; (b) are TSC-1 or TSC-2 deficient; (c) have overexpression of COX-1 or COX-2; (d) have lower levels of phosphos-Akt S473; (d) have higher levels of phosphos-MAPK; (e) have higher levels of phospho-S6 S235; (f) have increased production of prostaglandin; (g) insensitive to rapamycin; and (h) do do not have mTOR deregulation or hyperactivity; and if any is affirmative or positive, administering to the subject therapeutically effective amount of any composition or at least one COX inhibitor and/or an inhibitor of the prostaglandin biosynthesis pathway or described herein.

BRIEF DESCRIPTION OF THE DRAWINGS

FIGS. 1a-1i show the identification of an estrogen-induced prostaglandin biosynthesis signature in TSC2-deficient ELT3 cells and xenograft tumors.

FIG. 1a shows the cellular metabolites profile of ELT3 (Tsc2-deficient rat uterus-derived) cells treated with 10 nM estrogen for 24 hr. The cellular metabolites were profiled by mass spectrometry (n=5).

FIG. 1b shows the Box-plots of PGE2 and PGD2 based on the mass spectrometry profiles of ELT3 cells treated with estrogen.

FIG. 1c shows the immunoblot analysis of ELT3 cells treated with estrogen for 2, 4, or 24 hr. Beta-actin was used as a loading control.

FIG. 1d shows the secreted PGE2 levels measured in conditioned media collected from ELT3 cells treated with estrogen or control at the indicated times (n=3).

FIG. 1e shows the immunoblot analysis of 621-101 (LAM patient-derived) cells treated with estrogen for 0.5, 4, or 24 hr. Beta-actin was used as a loading control.

Figure if shows the secreted PGE2 levels measured in conditioned media collected from 621-101 cells treated with estrogen or control at the indicated times (n=3).

Figure 1A:
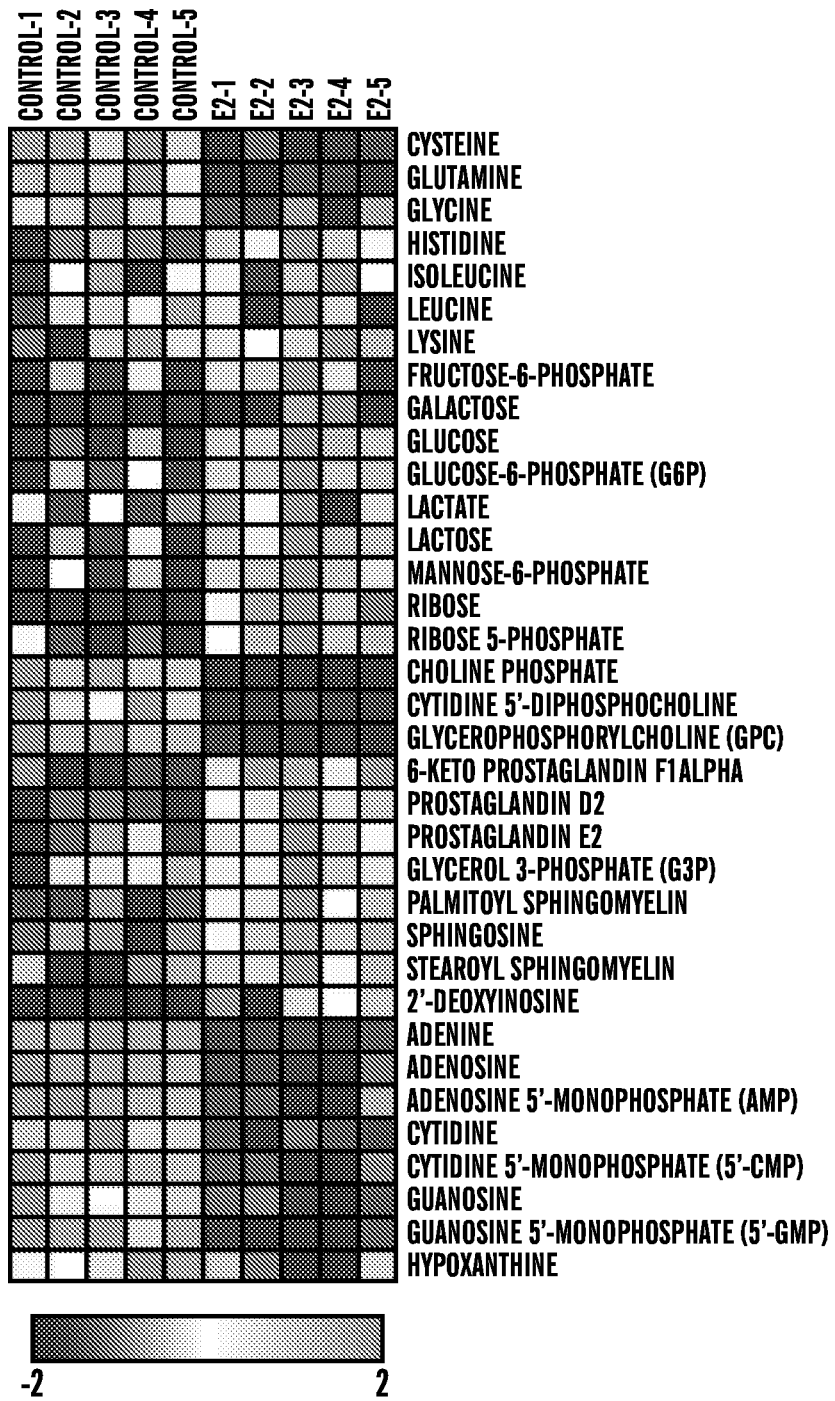
Figure 1E:
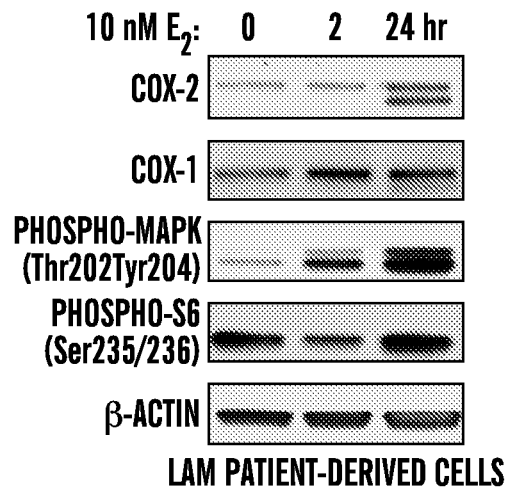
Figure 1F:
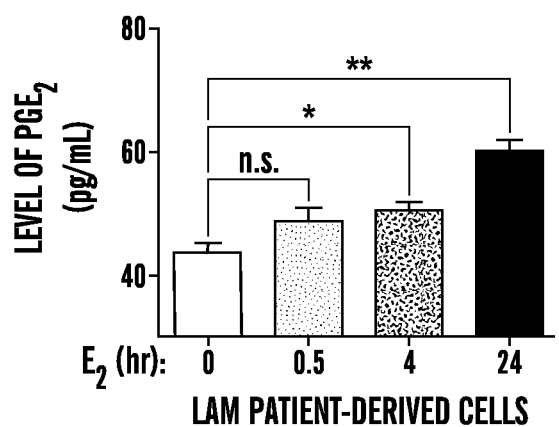
Figure 1G:
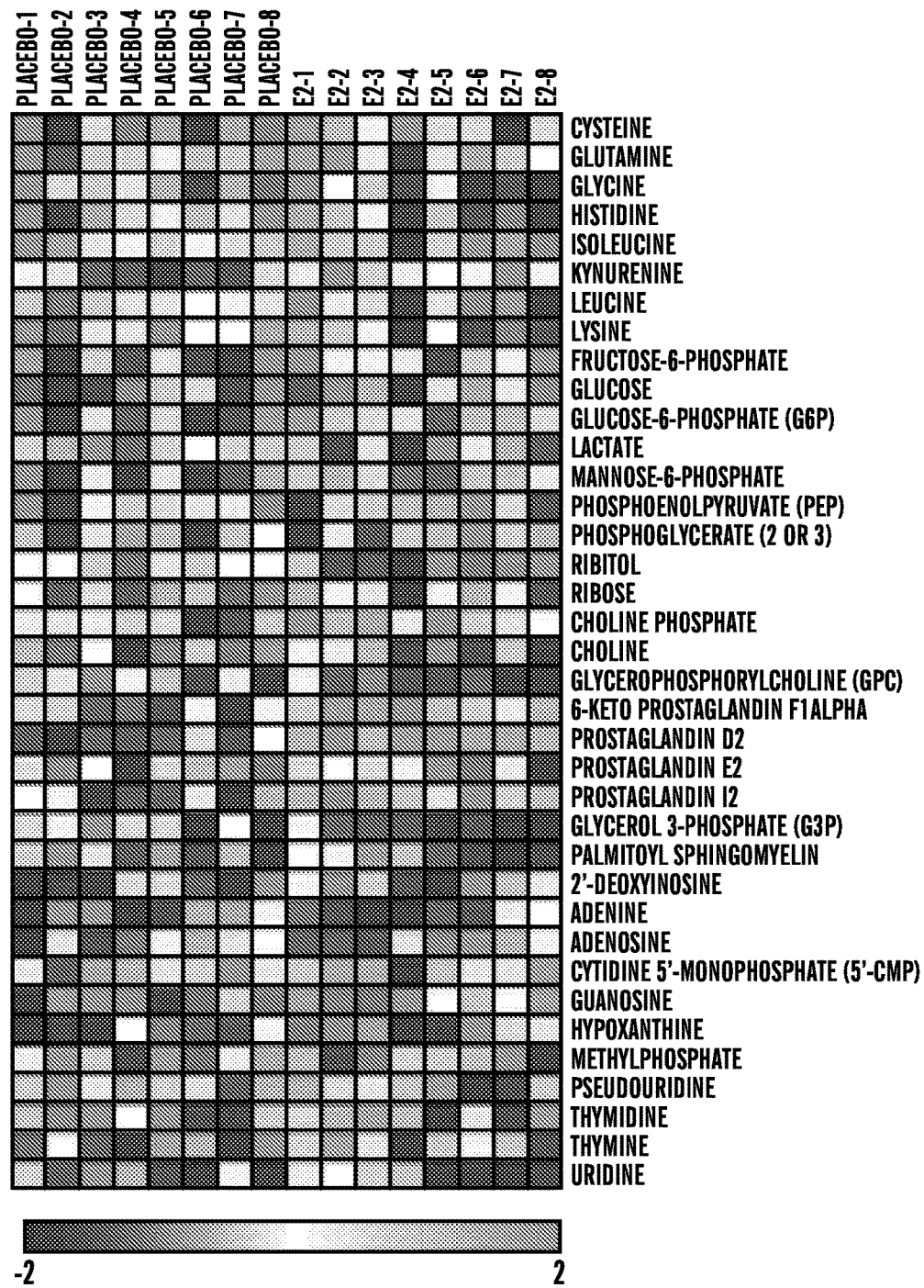

FIG. 1g shows the cellular metabolite profile of xenograft tumors from estrogen or placebo-treated mice. Cellular metabolites extracted from xenograft tumors from estrogen or placebo-treated mice and profiled by mass spectrometry (n=8).

Figure 1H:
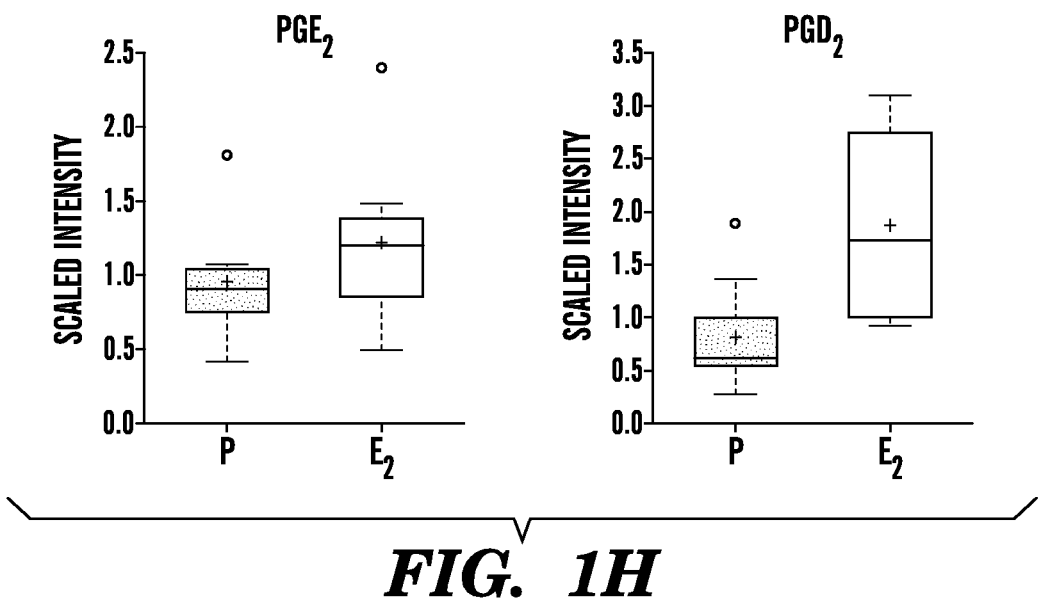

FIG. 1h shows the Box-plots of PGE2 and PGD2 obtained in the cellular metabolite profile of xenograft tumors from estrogen or placebo-treated mice.

Figure 1I:
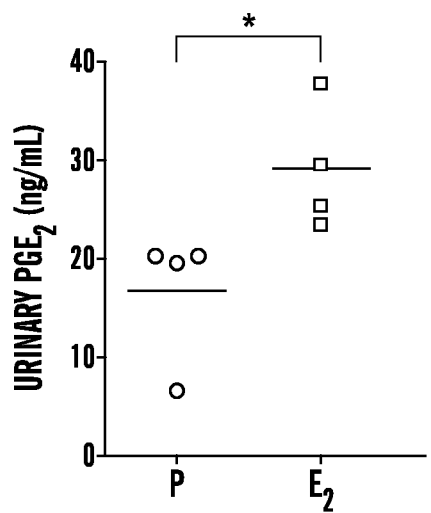

FIG. 1i shows the urinary PGE2 and creatinine from placebo or estrogen-implanted ovariectomized female mice bearing xenograft tumors was measured five-week post cell inoculation. PGE2 levels were normalized to creatinine. $*p<0.05$, $**p<0.01$.

FIGS. 2a-2l show that TSC2 negatively regulates COX-2 expression and prostaglandin production in a rapamycin-insensitive manner in vitro and in vivo.

Figure 2A:
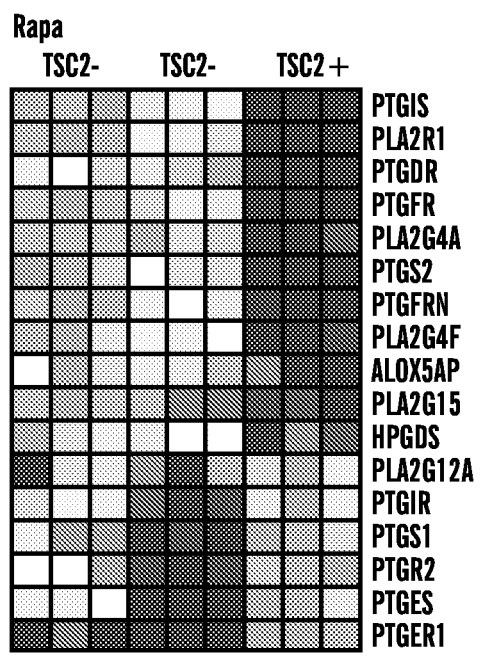

FIG. 2a shows the analysis of public expression data sets of TSC2-deficient LAM patient-derived and TSC2-reexpressing cells treated with 20 nM rapamycin or vehicle for 24 hours.

Figure 2B:
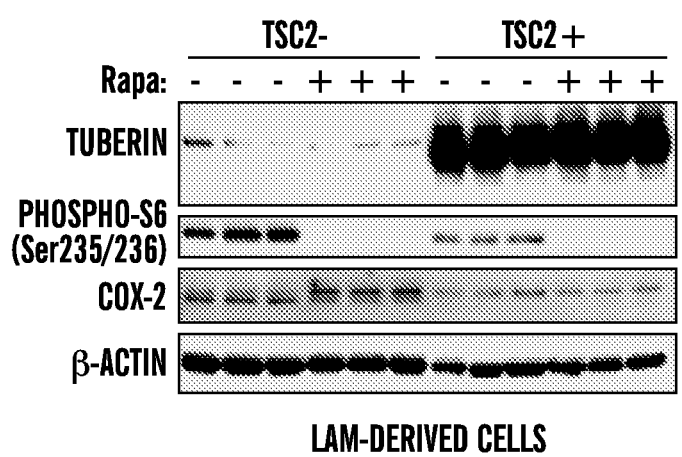

FIG. 2b shows the immunoblot analysis of tuberin, phospho-S6 (S235/236) and COX-2 protein in 621-101 cells.

Figure 2C:
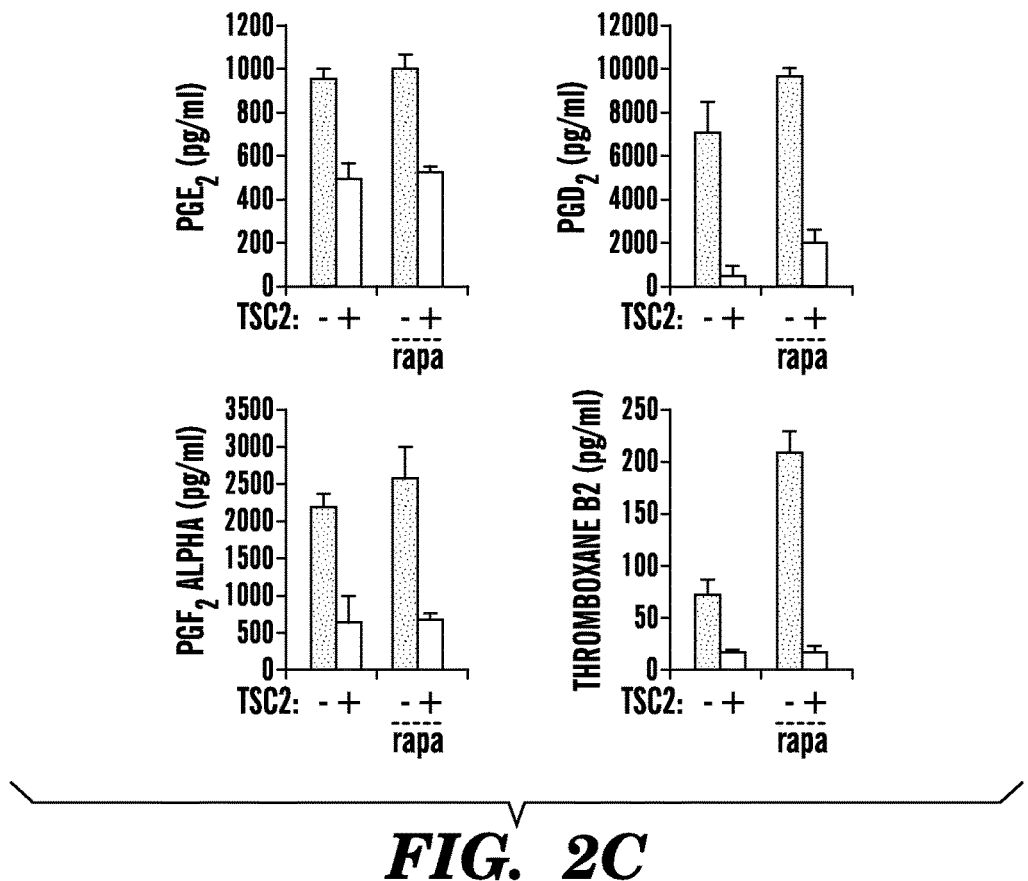

FIG. 2c shows the secreted prostaglandin levels quantified in conditioned media collected from 621-101 cells treated with 20 nM rapamycin for 24 hr or control (n=3).

Figure 2D:
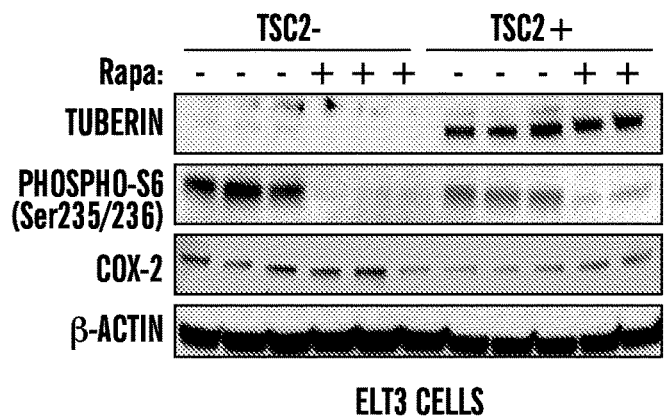

FIG. 2d shows the immunoblot analysis of tuberin, phospho-S6 (S235/236) and COX-2 protein in ELT3 cells.

Figure 2G:
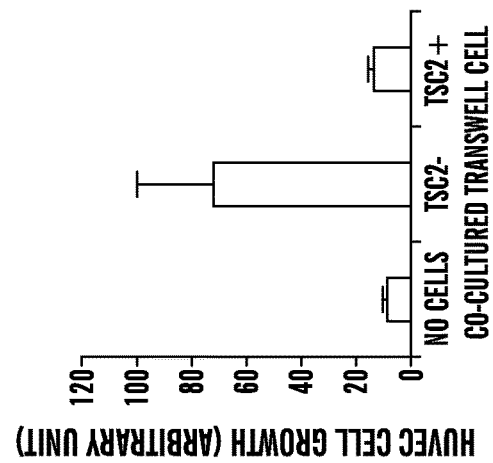
Figure 2F:
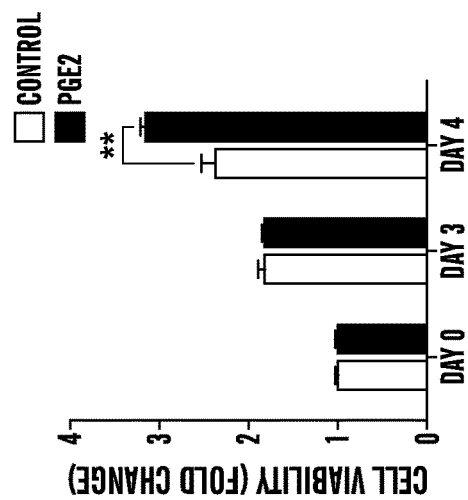
Figure 2E:
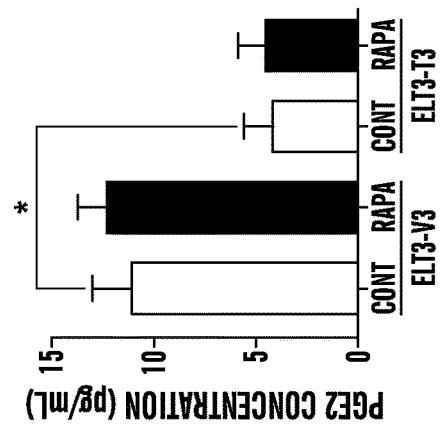

FIG. 2e shows the secreted prostaglandin levels quantified in conditioned media collected from ELT3 cells treated with 20 nM rapamycin for 24 hr or control (n=3).

FIG. 2f shows the cell variability of cells were treated with 500 nM PGE2 or vehicle for four days. Cell variability was measured using MTT assay.

FIG. 2g shows cell growth of HUVECs that were co-cultured with TSC2- or TC2+LAM patient-derived cells using 0.3 μM transwell inserts for 72 hr. Cell number was assayed using a fluorescent dye.

Figure 2H:
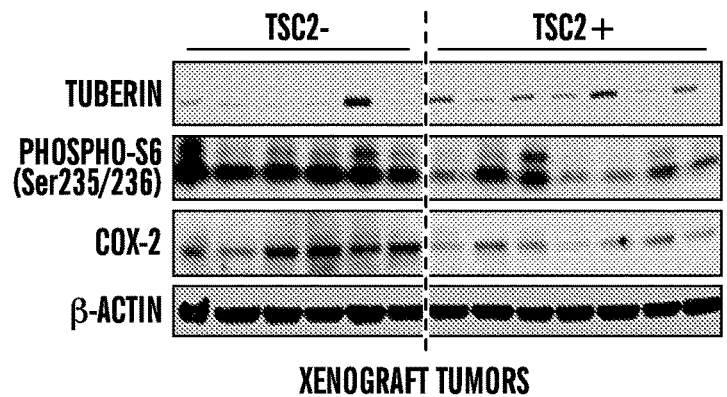

FIG. 2h shows the immunoblot analysis of tuberin, phospho-S6 (S235/236) and COX-2 in xenograft tumors of ELT3 cells. Female CB17-scid mice were inoculated with ELT3-V3 cells (TSC2-, vector addback) or TSC2 addback (TSC2+) ELT3-T3 cells subcutaneously.

Figure 2I:
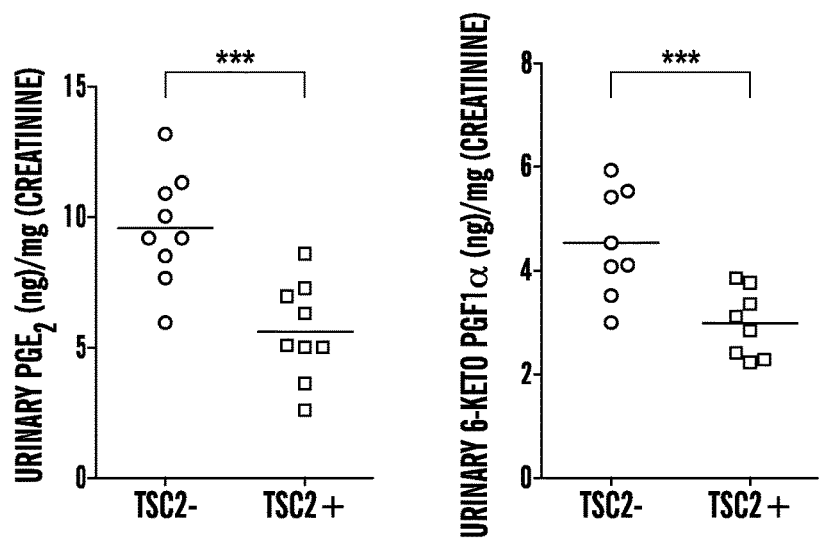

FIG. 2i shows the urinary levels of PGE2 and 6-keto-PGF1α normalized to creatinine levels in mice bearing xenograft tumors (n=9).

Figure 2J:
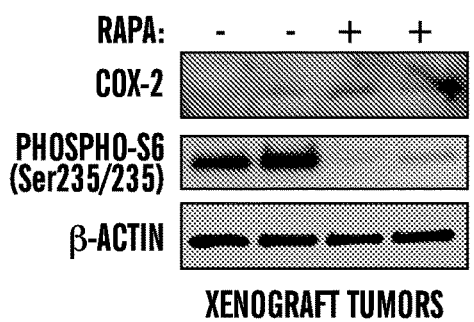

FIG. 2j shows the immunoblot analysis of phospho-S6 (S235/236) and COX-2 in xenograft tumors.

Figure 2K:
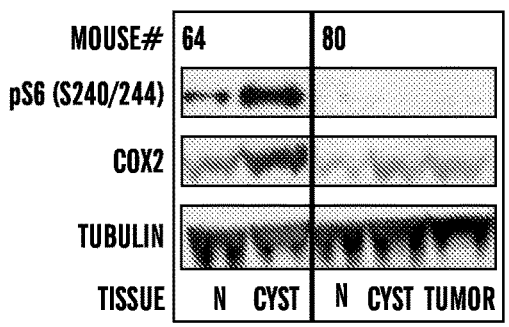

FIG. 2k shows the immunoblot analysis of phospho-S6 (S235/236) and COX-2 in TSC2+/−renal cystadenoma (Cyst). N denotes normal tissue.

Figure 2L:
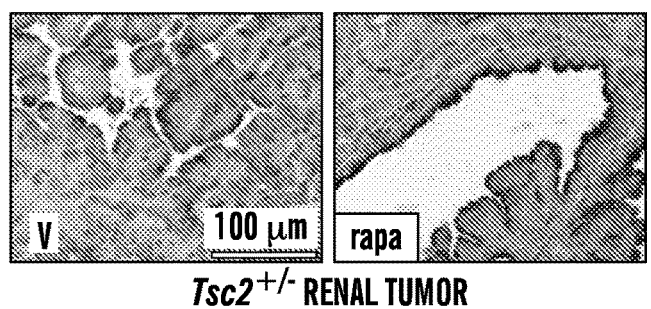

FIG. 2l shows the immunohistochemical staining of COX-2 in renal cystadenoma of Tsc2+/−mice treated with either vehicle or rapamycin. Scale bar, 100 μM. *p<0.05, p<0.01, *p<0.001.

FIGS. 3a-3g shows that aspirin treatment inhibits the growth of TSC2-deficient cells in vitro and in vivo, and reduces urinary levels of prostaglandins in vivo.

Figure 3:
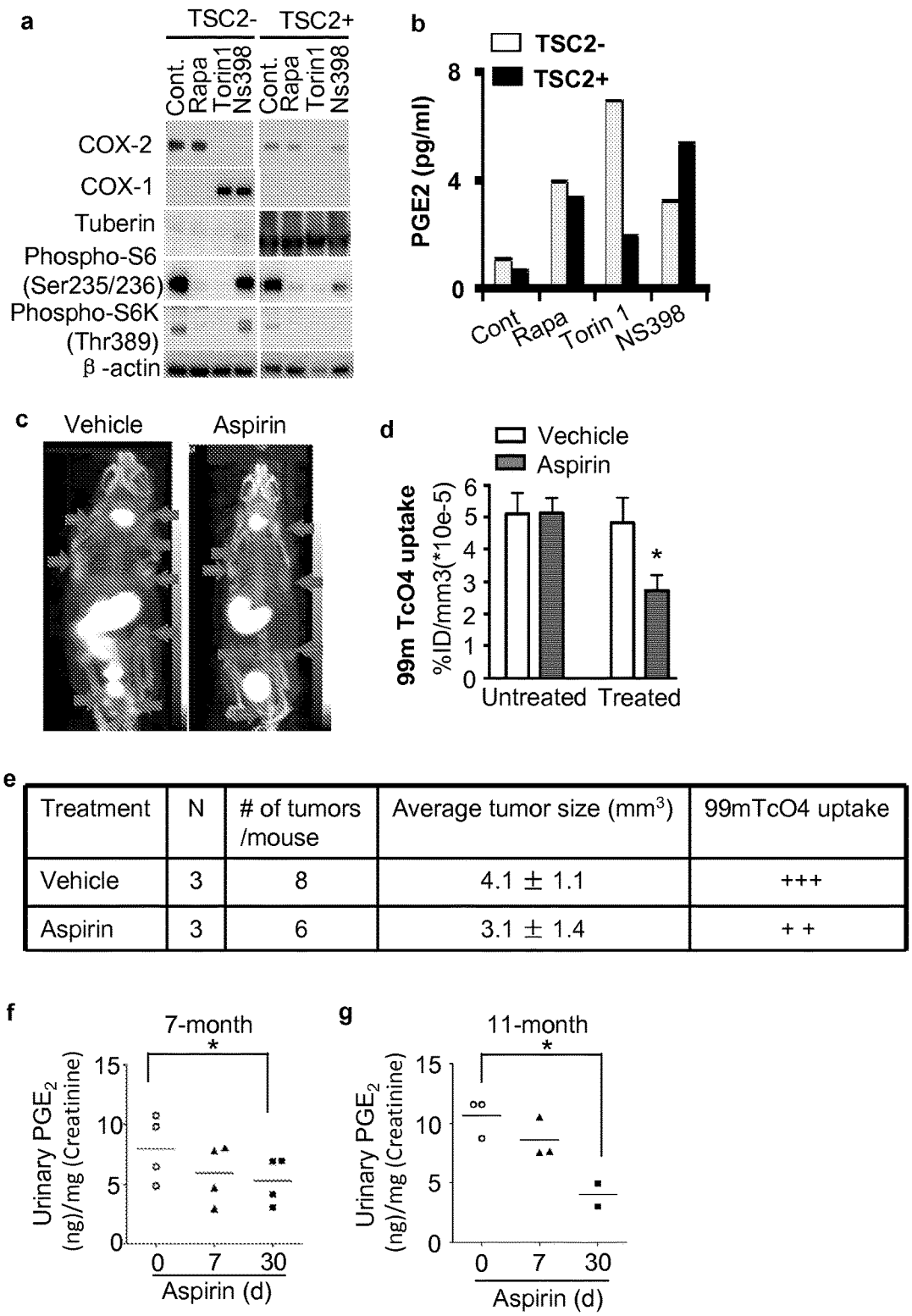

FIG. 3a shows the immunoblot of levels of COX-1, COX-2, phospho-p44/42 MAPK and phospho-S6 in 621-101 cells treated with 5 μM Sulindac, 50 μM NS398, or 450 μM aspirin for 24 hr. Levels of COX-1, COX-2, phospho-p44/42 MAPK and phospho-S6 were assessed by immunoblot.

FIG. 3b shows the PGE2 levels from conditioned media measured using ELISA.

FIG. 3c shows the location of TSC2-deficient LAM patient-derived cells that were intratracheally instilled into NCr nu/nu mice. SPECT/CT imaging shows tumor development seven months post-cell inoculation in mice treated with vehicle or aspirin for 30 days. Arrows indicate individual tumors.

FIG. 3d shows the tumor growth that was quantified using the radiotracer 99mTcO4-uptake (n=3). Bioluminescent imaging was performed weekly. Tumor area was normalized to the baseline before drug administration.

FIG. 3e shows the table summarizing the recorded tumor growth.

FIGS. 3f and 3g show the urinary PGE2 that was quantified from mice treated with aspirin or vehicle for 7 and 30 days. *p<0.05.

FIGS. 4a-4f shows the COX-2 expression and prostaglandin production in LAM nodules and LAM patients.

Figure 4:
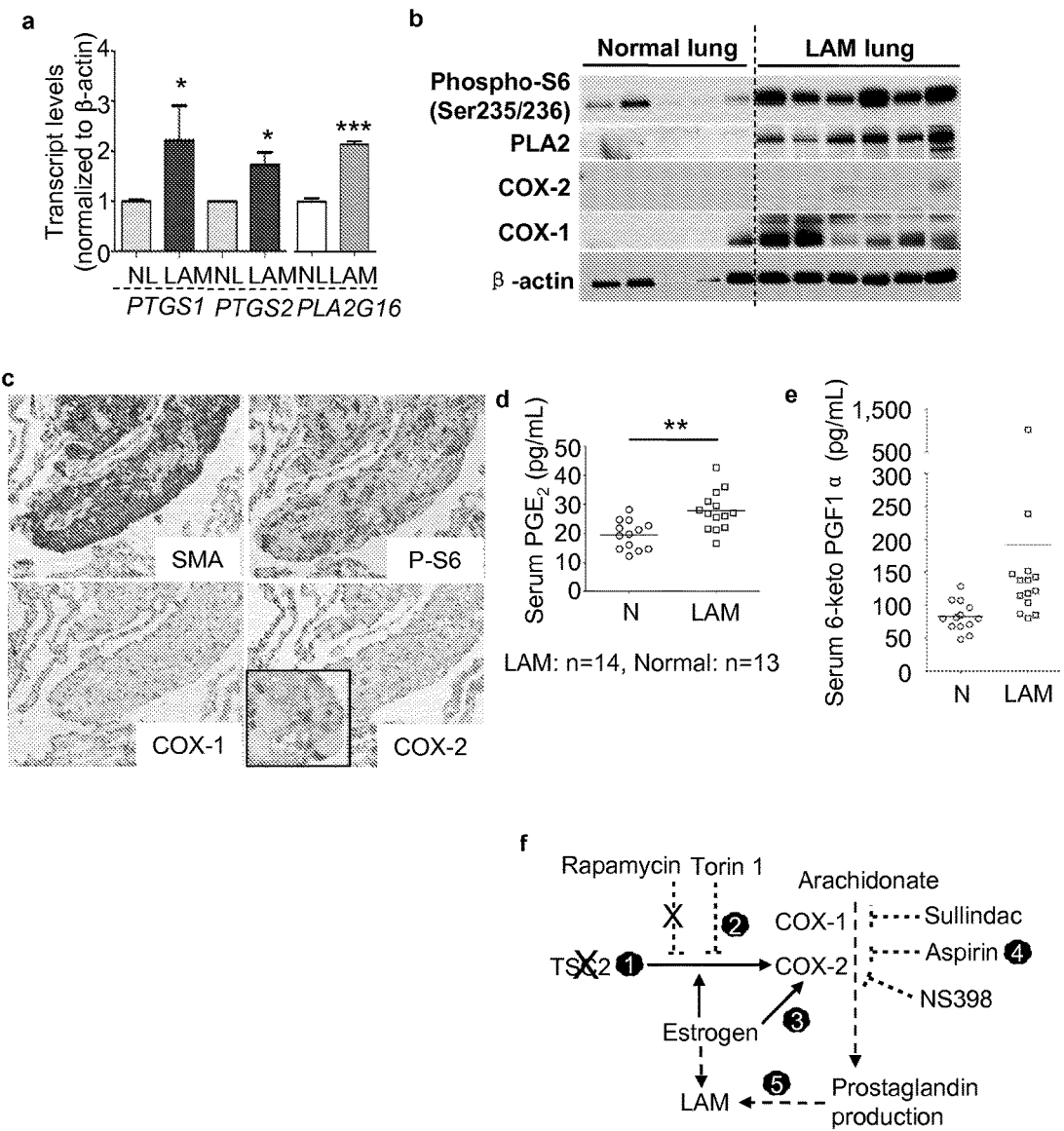

FIG. 4a shows the transcript levels of PTGS2 (COX-2) that were measured using real-time RT-PCR on RNA prepared from LAM lung and clinically normal lung samples (n=3 each).

FIG. 4b shows the levels of COX-1, COX-2, or PLA2 proteins from LAM or normal lungs (n=6) were determined by immunoblotting. Beta-actin was included as a loading control.

FIG. 4c shows LAM lung tissues stained with smooth muscle actin (SMA), phospho-S6 (P-S6) (S235/236), or COX-2 antibodies. Scale bar, 250 μM.

FIG. 4d shows serum levels of PGE2 in LAM (n=14) and healthy women (N) (n=13). *p<0.05.

FIG. 4e shows serum levels of 6-keto PGF1α in LAM (n=14) and healthy women (N) (n=13). *p<0.05.

FIG. 4f shows a schematic illustration of rapamycin-insensitive COX-2 activation and prostaglandin production in cells with mTORC1 activation. 1) TSC2 negatively regulates COX-2 expression and prostaglandin production; 2) Torin 1 suppresses COX-2 activation and prostaglandin production specifically to TSC2-deficient cells; 3) estrogen further increases COX-2 activation and prostaglandin production in TSC2-deficient cells; 4) Aspirin treatment suppresses tumor growth and prostaglandin production in a metastatic model of LAM; 5) LAM lesions express COX-2 and LAM patients have higher serum prostaglandins relative to healthy women, suggesting a potential biomarker for LAM.

Figure 5:
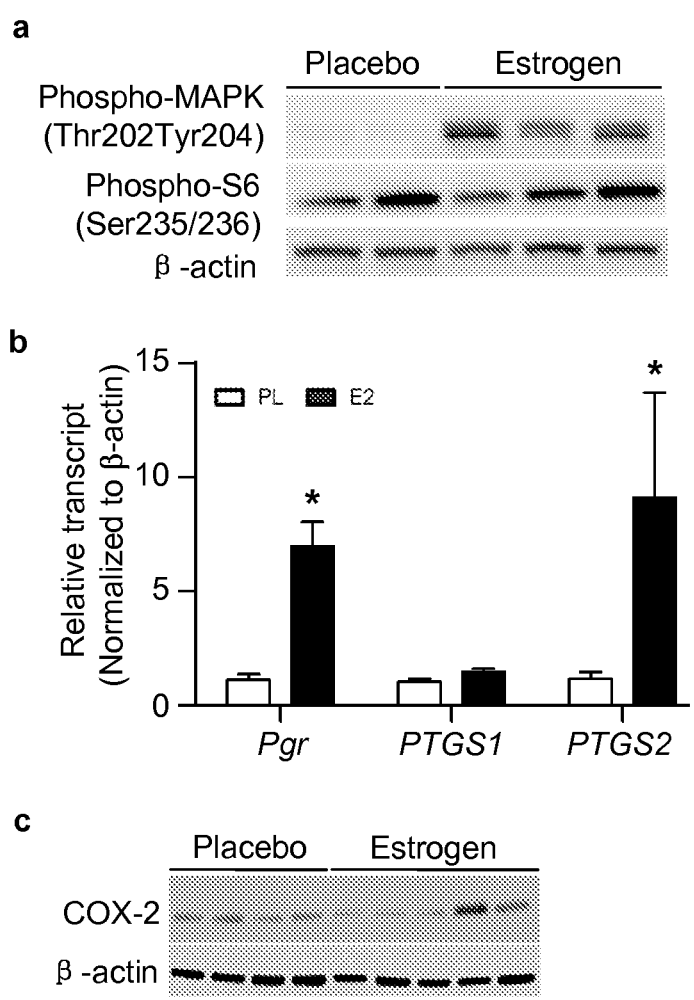

FIGS. 5a-5c show that estrogen increases COX-2 expression in a xenograft tumor model. TSC2-deficient ELT3 cells were subcutaneously injected into female ovariectomized mice implanted with estrogen or placebo pellets.

FIG. 5a shows the immunoblot analysis of phospho-MAPK (T202/Y204) and phospho-S6 (S235/236) in xenograft tumors (n=2-3) in host mice treated with estrogen and control vehicle.

FIG. 5b shows the transcript levels of Pgr (progesterone receptor), PTGS1 (COX-1) and PTGS2 (COX-2), were measured using real-time RT-PCR in primary tumors from placebo (PL) or estrogen-treated (E2) mice (n=3). *p<0.05.

FIG. 5c shows the immunoblot analysis of COX-2 levels in estrogen-treated xenograft tumor (n=4-5).

FIG. 6 shows a table of the analysis of published expression array shows upregulation of genes involved in prostaglandin biosynthesis.

Figure 7:
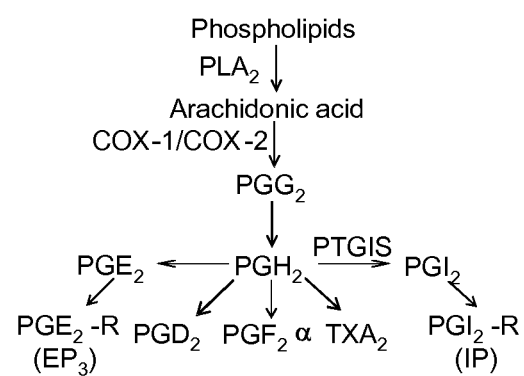

FIG. 7 shows the gene products that regulate prostaglandin biosynthesis in TSC2-deficient LAM patient-derived cells.

FIGS. 8a-8b show that rapamycin-insensitive expression of COX-2 and prostaglandin production in cells with mTORC1 activation.

FIG. 8a shows the immunoblot analysis of phospho-S6 (S235/236) and COX-2 protein in 293, HeLa, MCF-5 OVCAR-5 and U2OS cells treated with 20 nM rapamycin for 24 hr or control (n=3).

FIG. 8b shows the secreted prostaglandin levels quantified in conditioned media collected from 293, HeLa, MCF-5 OVCAR-5 and U2OS cells treated with 20 nM rapamycin for 24 hr or control (n=3).

Figure 9:
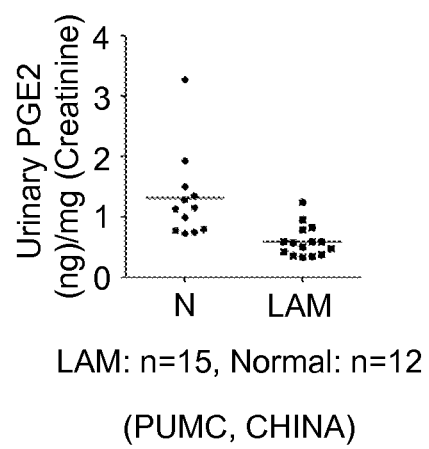

FIG. 9 shows the urinary levels of prostaglandins are not elevated in LAM patients. Urinary levels of 6-keto PGF1α and (b) PGE2 in LAM (n=4) and healthy women (N) (n=4) recruited at BWH were compared. (c) Urinary levels of PGE2 in LAM (n=15) and healthy women (N) (n=12) recruited at PUMC-China were compared.

DETAILED DESCRIPTION

Definitions

As used herein, the term "apoptosis" refers to a natural process of self-destruction in certain cells that is initiated and/or determined by activation of certain genes. Apoptosis can be initiated by an external stimulus e.g., administration of an inducer of apoptosis. Several biochemical events lead to characteristic cell changes (morphology) and death. These changes include, but are not limited to, cell blebbing, cell shrinkage, nuclear fragmentation, chromatin condensation, and chromosomal DNA fragmentation. Analysis of apoptosis can be performed by any method known in the art; non-limiting examples include cell free apoptotic assay, DNA fragmentation assay, DNA laddering assay, terminal transferase dUTP nick end labeling (TUNEL) assay and Annexin A5 (or annexin V) detection. The DNA can be labeled with propidium iodide or 7-AAD and analyzed by flow cytometry.

A "cancer" in a subject refers to the presence of cells possessing characteristics typical of cancer-causing cells, such as uncontrolled proliferation, immortality, metastatic potential, rapid growth and proliferation rate, loss of contact inhibition and certain characteristic morphological features. Often, cancer cells will be in the form of a tumor, but such cells may exist alone within a subject, or may be a non-tumorigenic cancer cell.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e., a metastatic tumor), a tumor also can be nonmalignant (i.e., non-metastatic tumor). Tumors are hallmarks of cancer, a neoplastic disease the natural course of which is fatal. Cancer cells exhibit the properties of invasion and metastasis and are highly anaplastic.

As used herein, the term "cancer therapy" refers to a therapy useful in treating cancer. In some embodiments, the cancer therapy involves the use of anti-cancer therapeutic agents and medical procedures. Non-limiting examples of cancer therapy and anti-cancer therapeutic agents include, but are not limited to, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN), anti-CD20 antibodies, an epidermal growth factor receptor (EGFR) antagonist (e.g., a tyrosine kinase inhibitor), HER1/EGFR inhibitor (e.g., erlotinib (TARCEVA)), platelet derived growth factor inhibitors (e.g., GLEEVEC™ (Imatinib Mesylate)), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

In one embodiment, "administration," "treating," and "treatment," as it applies to a subject, refers to the contact of an exogenous pharmaceutical, a drug, a compound, a therapeutic, or a composition to the subject. In another embodiment, "administration," "treating," and "treatment," as it applies to a subject, refers to the contact of any one of the described compounds or compositions to the subject.

Alternatively, the term "administering," refers to the placement of an inhibitor, a combination of compound, or a composition described herein for intended purposes such as treating LAM, inhibiting cell growth, killing cells or inducing apoptosis, into a subject by a method or route which results in at least partial localization of the inhibitors, the combination of compound, or the composition respectively at a desired site, i.e., cancer cells, tumor cells, tumor cells with TSC mutation(s) and/or overexpression of COX and/or prostaglandin production in the subject. The inhibitors, the combination of compounds, or the composition(s) described herein can be administered by any appropriate route which results in effective treatment of the subject, i.e. administration results in delivery to a desired location (e.g., directly to a tumor or near a tumor) in the subject where at least a portion of the inhibitors delivered. The period of time the inhibitors, the combination of compounds, or the composition(s) is/are active depends on the half-life in vivo after administration to a subject, and can be as short as a few hours, e.g., twenty-four hours, to a few days, to as long as several years. Modes of administration include injection, infusion, instillation, suppository (e.g., for vaginal, cervical, rectal or urethral insertion), percutaneous implantation or ingestion. "Injection" includes, without limitation, intravenous, intramuscular, intraarterial, intraventricular, intradermal, intraperitoneal, subcutaneous, subcuticular injection and infusion.

In one embodiment, as used herein, the term "treat" or "treatment" refers to reducing or alleviating at least one adverse clinical symptom associated with cancer, e.g., pain, swelling, tumor size, tumor growth rate, low blood count etc. In another embodiment, the term "treat" or "treatment" refers to slowing or reversing the progression of neoplastic uncontrolled cell multiplication, i.e., shrinking existing tumors and/or halting tumor growth. In another embodiment, the term "treat" or "treatment" refers to inducing apoptosis in cancer or tumor cells in the subject.

As used herein, the term "a therapeutically effective amount" or "an effective amount" refers to an amount sufficient to achieve the intended purposes such as treating cancer, inhibiting cell growth, killing cells or inducing apoptosis. In one embodiment, a therapeutically effective amount of a compound, a combination of compounds, a pharmaceutical formulation, or a composition described herein for a method of treating cancer or TSC is an amount of sufficient to induce apoptosis of cancer cells of the subject as compared to the level of apoptosis/cell death in the absence of the compound, the combination of compounds, the pharmaceutical composition/formulation or the composition. In other embodiments, the amount of the composition administered is preferably safe and sufficient to treat, delay the development of a tumor, and/or delay further growth of the tumor. In some embodiments, the amount can thus cure or result in amelioration of the symptoms of cancer and tumor growth, slow the course of cancer progression, slow or inhibit a symptom of cancer, slow or inhibit the establishment of secondary symptoms of cancer or inhibit the development of a secondary symptom of the cancer. For example, an effective amount of a compound, a combination of compounds, or a composition described herein inhibits further tumor growth (e.g., LAM or AML), cause a reduction in size or even completely halt tumor growth, shrink the size of a tumor(s), even initiate complete regression of tumor, and reduce clinical symptoms associated with a tumor. In one embodiment, an effective amount for treating cancer or TSC is an amount of a compound, a combination of compounds, or a composition described herein sufficient to result in a reduction or complete removal of the symptoms of the disorder, disease, or medical condition. In another embodiment, an effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount." However, for any given case, an appropriate "effective amount" can be determined by a skilled artisan according to established methods in the art using only routine experimentation.

Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include radioactively labeled derivatives of the compounds described herein (e.g., biotin or avidin, with enzymes such as horseradish peroxidase and the like, with bioluminescent agents, chemoluminescent agents or fluorescent agents). Additionally, moieties can be added to the compounds described herein or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of the compound or class, are also contemplated herein. In one embodiment, the term "derivatives", as used herein, also encompasses prodrugs of the compounds described herein, which are known to enhance numerous desirable qualities of pharmaceuticals (e.g., solubility, bioavailability, manufacturing, etc.).

The term "analogue" or "analog", as used herein, refers to a chemical compound having a structure similar to that of another but differing from it in respect to a certain component, e.g., it can have a similar action metabolically. In one embodiment, an analog is a drug that is similar to the drug from which it is derived.

As used herein, the terms "drug" and "compound" are used interchangeably and they refer to a known drug described herein.

As used herein, the term "mTOR deregulation" with respect to cancer cells or cells with neoplasia refers to increased or decreased signaling of the mTOR pathway compared to normal cells or cells without neoplasia. Increased or decreased signaling can be analyzed by any method known in the art, e.g., by monitoring the corresponding increase or decrease phosphorylation of the mTOR downstream effectors molecules S6K1 and 4E-BP1. See L. Yan, 2006 J. Biol. Chem., 281: 19793-19797.

As used herein, the term "mTOR hyperactivation" with respect to cancer cells or cells with neoplasia refers to increased signaling of the mTOR pathway compared to normal cells or cells without neoplasia. Increased mTOR signaling can be analyzed by any method known in the art, e.g., by monitoring the increase phosphorylation of the mTOR downstream effectors molecules S6K1 and 4E-BP1. See L. Yan, 2006 J. Biol. Chem., 281: 19793-19797.

As used herein, the term "neoplasia" refers to the abnormal proliferation of benign or malignant cells.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

As used herein the term "cell proliferation" or "cell growth" refers to reproduction and increase in cell number, i.e., cell division.

As used herein in the context of a level of mTOR deregulation or hyperactivity, a "detectable level" refers to a level of deregulation and/or hyperactivity in a sample that allows the regulation and/or activity of mTOR to be distinguished from a reference level, e.g. the regulation and/or activity of mTOR in a reference level (e.g., mTOR activity in a cancer free sample), by at least one of the methods and/or assays for mTOR regulation and/or activity described elsewhere herein. In some embodiments, a detectable level of mTOR hyperactivity can be a level of mTOR activity at least 10% greater than a reference level, e.g. 10% greater, 20% greater, 50% greater. 100% greater, 200% greater, or 300% or greater.

As used herein the term "comprising" or "comprises" is used in reference to compositions, methods, and respective component(s) thereof, that are essential to the disclosure, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of this disclosure.

The term "consisting of" refers to compositions, methods, and respective components thereof as described herein, which are exclusive of any element not recited in that description of the embodiment.

Unless otherwise explained, all technical and scientific terms used herein have the same meaning as commonly understood by one of ordinary skill in the art to which this disclosure belongs. Definitions of common terms in molecular cell biology may be found in Harvey Lodish et al., Molecular Cell Biology, 6$^{th}$ edition, published by W. H. Freeman and Company, 2007 (ISBN 0716776014); Kendrew et al. (eds.), The Encyclopedia of Molecular Biology, published by Blackwell Science Ltd., 1994 (ISBN 0716776014); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the technology and embodiments thereof presented herein can be performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Immunology (CPI) (John E. Coligan, et. al., ed. John Wiley and Sons, Inc.), Current Protocols in Cell Biology (CPCB)

(Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), and Methods in Molecular biology, Vol. 180, Transgenesis Techniques by Alan R. Clark editor, second edition, 2002, Humana Press, which are all herein incorporated by reference in their entireties.

It should be understood that this technology is not limited to the particular methodology, protocols, and reagents, etc., described herein and as such may vary. The terminology used herein is for the purpose of describing particular embodiments only, and is not intended to limit the scope of the present technology, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present technology. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The methods and compositions provided herein relate, in part, to the discovery of cancer cells and tumors of LAM are responsive to aspirin; they decreased in size and reduced proliferation when treated with aspirin. The inventors observed that the expression of cyclooxygenase-2 (COX-2) and prostaglandin production are elevated in a rapamycin-insensitive and Torin1-sensitive manner in TSC2-deficient cells, but not in TSC2-reexrpessing cells. Cells having a mutation in the TSC2 locus are deficient in TSC2 or tuberin.

The inventors have discovered previously that estrogen increases levels of circulating tumor cells and pulmonary metastases of tuberin-deficient cells in a xenograft model of LAM. Studies have demonstrated that estrogen induces COX-2-mediated prostaglandin synthesis. COX-2 is a rate-limiting enzyme catalyzing the conversion of arachidonate to prostaglandins. COX-2 overexpression has been documented in human tumors, and prostaglandins may contribute to cancer development. Here, the inventors discovered that estrogen enhances prostaglandin production in TSC2-deficient cells. Surprisingly, loss of TSC2 increases COX-2 and prostaglandin biosynthesis in a rapamycin-insensitive manner, indicatting an mTORC1-independent pathway in LAM in addition to the mTORC1 pathway. Aspirin suppresses tumor progression in a xenograft tumor model. In a metastatic tumor model, Aspirin treatment decreased the growth of tumors of LAM derived cells, correlated with reduction of urinary prostaglandins. Quantitative measurement revealed that LAM patients have significantly higher serum levels prostaglandins compared with healthy women. Aspirin treatment improved lung function and reduced prostaglandin levels in exhaled breath condensate in LAM patients. This study indicates that targeting COX-2 with aspirin or related drugs and/or targeting the prostaglandin biosynthetic pathway would have therapeutic benefit in LAM and TSC-related diseases.

Treatment Methods of Lymphangioleiomyomatosis (LAM).

Accordingly, provided herein is a method for treating LAM in a subject in need thereof comprising administering to a subject therapeutically effective amount of a cyclooxygenase (COX) inhibitor and/or an inhibitor of the prostaglandin biosynthetic pathway.

In one embodiment, provided herein is a method for treating LAM in a subject in need comprising selecting a subject having LAM and administering to the subject therapeutically effective amount of a COX inhibitor or an inhibitor of the prostaglandin biosynthetic pathway.

In one embodiment, provided herein is a method for treating LAM in a subject in need comprising selecting a subject having LAM and has a mutation in the TSC locus, and administering to the subject therapeutically effective amount of a COX inhibitor or an inhibitor of the prostaglandin biosynthetic pathway.

In one embodiment, provided herein is a method for treating LAM in a subject in need comprising selecting a subject having cancer cells that are TSC-1 or TSC-2 deficient or both TSC1/2 deficient and administering to the subject therapeutically effective amount of a COX inhibitor or an inhibitor of the prostaglandin biosynthetic pathway.

In one embodiment, provided herein is a method for treating LAM in a subject in need comprising selecting a subject having COX overexpression and administering to the subject therapeutically effective amount of a COX inhibitor or an inhibitor of the prostaglandin biosynthetic pathway.

In one embodiment, provided herein is a method for treating LAM in a subject in need comprising selecting a subject having increased prostaglandin production and administering to the subject therapeutically effective amount of a COX inhibitor or an inhibitor of the prostaglandin biosynthetic pathway.

In one embodiment, provided herein is a method for treating LAM in a subject in need comprising selecting a subject having a mutation in the TSC locus and having a COX overexpression and/or increased prostaglandin production, and administering to the subject therapeutically effective amount of a COX inhibitor or an inhibitor of the prostaglandin biosynthetic pathway.

In one embodiment, provided herein is a method for treating LAM in a subject in need comprising selecting a subject having LAM and having a COX overexpression and/or increased prostaglandin production, and administering to the subject therapeutically effective amount of a COX inhibitor or an inhibitor of the prostaglandin biosynthetic pathway.

In one embodiment, provided herein is a method for treating LAM in a subject in need comprising selecting a subject having a mutation in the TSC locus and having increased prostaglandin production, and administering to the subject therapeutically effective amount of a COX inhibitor or an inhibitor of the prostaglandin biosynthetic pathway.

In one embodiment, provided herein is a method for treating LAM in a subject in need comprising selecting a subject having LAM and having increased prostaglandin production and administering to the subject therapeutically effective amount of a COX inhibitor or an inhibitor of the prostaglandin biosynthetic pathway.

In one embodiment, provided herein is a method for treating LAM in a subject in need comprising and having selecting a subject having a mutation in the TSC locus and having a COX overexpression, and administering to the subject therapeutically effective amount of a COXinhibitor or an inhibitor of the prostaglandin biosynthetic pathway.

In one embodiment, provided herein is a method for treating LAM in a subject in need comprising and having selecting a subject having having LAM and having a COX overexpression, and administering to the subject therapeutically effective amount of a COXinhibitor or an inhibitor of the prostaglandin biosynthetic pathway.

In one embodiment, provided herein is a method for treating LAM in a subject in need comprising first determining whether the subject has one or more of the following: (a) a COX overexpression; (b) a mutation in the TSC locus; (c) increased prostaglandin production; (d) mTOR deregulation or hyperactivity ie., normal mTOR regulation or activity; and (e) at least one cancer cell that is insensitive to rapamycin; and if any is affirmative or positive, administering to the subject therapeutically effective amount of a COX inhibitor or an inhibitor of the prostaglandin biosynthetic pathway.

In one embodiment, provided herein is a method for treating LAM in a subject in need comprising first determining whether the cancer cells of the subject has one or more of the following features:(a) a mutation in the TSC locus; (b) are TSC-1 or TSC-2 deficient; (c) have overexpression of COX-1 or COX-2; (d) have lower levels of phosphos-Akt S473; (d) have higher levels of phosphos-MAPK; (e) have higher levels of phospho-S6 S235; (f) have increased production of prostaglandin; (g) insensitive to rapamycin; and (h) do do not have mTOR deregulation or hyperactivity; and if any is affirmative or positive, administering to the subject therapeutically effective amount of any composition or at least one COX inhibitor and/or an inhibitor of the prostaglandin biosynthesis pathway or described herein.

In one embodiment, provided herein is a method for treating LAM in a subject in need comprising selecting a subject who has the cancer cells that have one or more of the following features:(a) a mutation in the TSC locus; (b) are TSC-1 or TSC-2 deficient; (c) have overexpression of COX-1 or COX-2; (d) have lower levels of phosphos-Akt S473; (d) have higher levels of phosphos-MAPK; (e) have higher levels of phospho-S6 S235; (f) have increased production of prostaglandin; (g) insensitive to rapamycin; and (h) do do not have mTOR deregulation or hyperactivity; and if any is affirmative or positive, administering to the subject therapeutically effective amount of any composition or at least one COX inhibitor and/or an inhibitor of the prostaglandin biosynthesis pathway or described herein.

In one embodiment of any method described herein, the method further comprises selecting a subject who has TSC or has been diagnosed with a mutation at the TSC loci. The subject can be genetically screened for TSC. A skilled physician will be able to differentially diagnosis TSC using medical diagnostic methods known within the art.

In one embodiment of any method described herein, the subject is a mammal. In another embodiment, the subject is a primate mammal. In one embodiment of any method described, the subject is human.

In one embodiment of any method described, the method further comprises determining whether the subject has a negative mutation in the TSC locus. In one embodiment, the TSC1 or TSC2 or both TSC1 and TSC2 have at least one negative mutation.

In one embodiment of any method described, the method further comprises selecting the subject a negative mutation in the TSC locus.

In one embodiment of any method described, the method further comprising determining whether the cancer cells of the subject are TSC-1 or TSC-2 deficient.

In one embodiment of any method described, the method further comprises selecting the subject having cancer cells that are TSC-1 or TSC-2 deficient.

In one embodiment of any method described, the method further comprises selecting the subject having COX-1 or COX-2 overexpression.

In one embodiment of the method described, the method further comprises selecting the subject having increased prostaglandin production.

In one embodiment of any method described herein, a tumor in the subject being treated is reduced in size by at least 5%.

In one embodiment of any method described herein, the subject being treated has a reduction in prostaglandin production by at least 5%.

In one embodiment of any method described herein, the subject being treated has a reduction in COX overexpression by at least 5%.

In one embodiment of any method described herein, the subject being treated has an improvement of lung function by at least 5%.

In one embodiment of any method described, the subject has a mutation in the TSC locus. In one embodiment, the mutation is at TSC 1 or TSC2 or at both TSC1 and TSC2. In one embodiment, the mutation is a negative mutation that results in reduced or decrease functional protein expression, for example, prematurely translation that give rise to a truncated protein.

In one embodiment of any method described, the subject has a mutation in at least one of the TSC loci. In one embodiment of any method described, the cancer cells or tumor obtained from the subject to be treated involves mutations in at least one of the TSC loci. In one embodiment, the mutation is at the TSC1 locus. In another embodiment, the mutation is at the TSC2 locus. In another embodiment, the mutation is at both the TSC1 and TSC2 loci.

In one embodiment of any method described, the cancer cells of the subject are TSC-1 or TSC-2 deficient. In other words, the subject is hamartin-deficient or tuberin-deficient. Negative mutations in the TSC1 and TSC2 that result in hamartin-deficiency or tuberin-deficiency are known in the art, eg. small deletions or insertions of DNA in the TSC gene that create a premature stop signal in the transcribed mRNA. These mutations can be determined by any method known in the art, eg. DNA sequencing. Hamartin-deficient or tuberin-deficient status of cells can be determined by any method known in the art, e.g., immunoassays.

In one embodiment of any method described, the subject has a COX overexpression. In one embodiment, the COX overexpression is a COX-1 or COX-2 overexpression. Cyclooxygenase (COX), also known as prostaglandin-endoperoxide synthase (PTGS), is an enzyme (EC 1.14.99.1) that is responsible for formation of important biological mediators called prostanoids, including prostaglandins, prostacyclin and thromboxane. Overexpression of COX-1 or COX-2 can be determined by any method known in the art, e.g., by quantitative RT-PCR or Western blot analysis or immunoassays as described in the Example.

In one embodiment of any method described, the cancer cells of the subject are TSC-1 or TSC-2 deficient, and have overexpression of COX-1 or COX-2.

In one embodiment of any method described, the cancer cells of the subject have lower levels of phosphos-Akt 5473 by at least 5% compared to control cells from a healthy subject or control reference for phosphos-Akt S473 in health cells. In some other embodiments, the cancer cells of the subject have lower levels of phosphos-Akt S473 by at least 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more than a control healthy subject or a control reference for phosphos-Akt S473 in health cells.

In one embodiment of any method described, the cancer cells of the subject have higher levels of phosphos-MAPK or phospho-S6 by at least 5% compared to control cells from a healthy subject or control reference for phosphos-MAPK or phospho-S6 S235 respectively in health cells. In some other embodiments, the cancer cells of the subject have lower levels phosphos-MAPK or phospho-S6 S235 by at least 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more than a control healthy subject or a control reference for phosphos-MAPK or phospho-S6 S235 respectively in health cells.

In one embodiment of any method described, the cancer cells of the subject are TSC-1 or TSC-2 deficient, and have lower levels of phosphos-Akt S473 by at least 5% compared to control cells from a healthy subject or control reference for phosphos-Akt S473 in health cells.

In one embodiment of any method described, the cancer cells of the subject are TSC-1 or TSC-2 deficient, and have higher levels of phosphos-MAPK or phospho-S6 S235 by at least 5% compared to control cells from a healthy subject or control reference for phosphos-MAPK or phospho-S6 S235 respectively in health cells.

In one embodiment of any method described, the cancer cells of the subject are TSC-1 or TSC-2 deficient, have lower levels of phosphos-Akt S473 and have higher levels of phosphos-MAPK or phospho-S6 S235.

In one embodiment of any method described, the cancer cells of the subject are TSC-1 or TSC-2 deficient, have lower levels of phosphos-Akt S473 and have higher levels of phosphos-MAPK or phospho-S6 S235.

In one embodiment of any method described, the cancer cells of the subject are TSC-1 or TSC-2 deficient, have overexpression of COX-1 or COX-2, have lower levels of phosphos-Akt S473 and have higher levels of phosphos-MAPK or phospho-S6 S235.

In some embodiments, the overexpression of COX-1 or COX-2 is increased by at least 5%, at least 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more than a control subject or a control reference for COX-1 or COX-2 respectively. In one embodiment, the control subject is one who does not have LAM and/or is not TSC1- or TSC2-deficient. In one embodiment, the control reference for COX-1 or COX-2 expression level is the level obtained for health subjects. For example, the average amount of COX-1 or COX-2 found in a population of health subjects not having been diagnosed with LAM and/or TSC 1 or 2 deficient or cells obtain therefrom.

In one embodiment of any method described, the subject has increased prostaglandin production. Prostaglandins are products of cyclooxygenases (COX-1/COX-2). The prostaglandins are a group of lipid compounds that are derived enzymatically from fatty acids and have important functions in the animal body. Every prostaglandin contains 20 carbon atoms, including a 5-carbon ring. Prostaglandins can be determined by any method known in the art, e.g., by using enzyme immunoassay kits as described in the Example.

In one embodiment of any method described, the prostaglandins include but are not limited to prostaglandin E1 (PGE1 or PGE1), prostaglandin I2 (PGI2 or PGI2) and rostaglandin E2 (PGE2 or $PGE_2$).

In one embodiment of any method described, the prostaglandin level is determined from a biological sample obtained from the subject, e.g., a body fluid of the subject. Examples of bodily fluids that can be obtained for the measuring the prostaglandin level include but are not limited to a blood sample, a peritoneal sample, a urine sample, a bladder sample and a sweat sample. In another embodiment, the biological sample is a blood sample. In one embodiment, the blood sample is a plasma sample or a serum sample.

In some embodiments, the increased in prostaglandin production is at least 5%, at least 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more than a control subject or a control reference for the respective prostaglandins analysed. In one embodiment, the control subject is one who does not have LAM and/or TSC 1 or 2 deficient. In one embodiment, the control reference for prostaglandin is the level obtained for health subjects. For example, the average amount of the respective prostaglandin found in a population of health subjects not having been diagnosed with LAM and/or TSC 1 or 2 deficient.

In one embodiment of any method described, the subject is tested to determine whether the subject has at least one cancer cell that is insensitive to rapamycin.

In one embodiment of any method described, at least one cancer cell of the subject is insensitive to rapamycin. For example, a sample of cancer cells or tumor is excised from the subject in a biopsy. The sample can then be contacted with rapamycin ex vivo or in vitro and monitored for the effect of rapamycin on apoptosis and cell proliferation of the cancer cells or tumor cells. Alternatively, the sample can be explanted into a host subject, e.g., a mouse or rat, the host subject is treated with rapamycin and monitored for the effect of rapamycin on changes in sample size, growth etc. of the explanted sample.

In some embodiment, "insensitive to rapamycin" means that treatment of the cancer cell with rapamycin does improve correct the overexpression of COX-1 or COX-2, increased production of prostaglandin, lower levels of phosphos-Akt S473 and higher levels of phosphos-MAPK or phospho-S6 S235.

In one embodiment, if there is no or neglible observable decrease in sample size or growth or weight of the explanted sample or tumor, the subject has at least one cancer cell that is insensitive to rapamycin. In one embodiment, if there is no or neglible observable increase in apoptosis and/or decrease in cell proliferation of cancer or tumor cells contacted in ex vivo or in vitro, the subject has at least one cancer cell that is insensitive to rapamycin.

In another embodiment, if there is observable increase in sample size or growth or weight of the explanted sample or tumor, the subject has at least one cancer cell that is insensitive to rapamycin. In one embodiment, if there is no or neglible observable increase in cell proliferation of cancer or tumor cells contacted in ex vivo or in vitro, the subject has at least one cancer cell that is insensitive to rapamycin.

In some embodiment, no or neglible observable decrease in sample size or growth, or decrease in cell proliferation of cancer or tumor cells means a decrease less than 5.0%, less than 4.5%, less than 4.0%, less than 3.5%, less than 3.0%, less than 2.5%, less than 2.0%, less than 1.5%, less than 1.0%, less than 0.5%, less than 0.1% or 0% compared to control cancer cells not contacted with rapamycin or control host subject not treated with rapamycin.

In one embodiment, no or neglible observable decrease in sample size or growth means no detectable significant differences in the changes in the size or weight of the explanted samples in the rapamycin-treated host subject compared to non-rapamycin treated control host subject.

In some embodiment, no or neglible observable increase in apoptosis means an increase less than 5.0%, less than 4.5%, less than 4.0%, less than 3.5%, less than 3.0%, less than 2.5%, less than 2.0%, less than 1.5%, less than 1.0%, less than 0.5%, less than 0.1% or 0% compared to control cancer cells not contacted with rapamycin.

In one embodiment, an observable increase in increase in sample size or growth or weight of the explanted sample or tumor, or cell proliferation of cancer cells means at least 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more than a control cancer cells or control host subject not treated with rapamycin.

In one embodiment of any method described, at least one cancer cell of the subject does not involve mTOR deregulation or hyperactivity.

The mTOR signaling pathway is a major player in controlling cell growth and cell division. Cancers associated with genetic defects often have aberrant mTOR signaling. Some LAM cells have TSC mutations. A subset of LAM occurs in conjunction with mutations in TSC2, which encodes the protein tuberin (TSC2). The TSC1/TSC2 heterodimer, through inhibition of the Ras homolog enriched in the brain protein (Rheb), negatively regulates the mammalian target of rapamycin (mTOR) complex 1 (TORC1). Therefore, LAM patient lesions have hyperactivation of TORC1. Rapamycin is a naturally occurring macrolide that inhibits TORC1 actively and is effective in shrinking kidney angio myolipomas (AML).

In one embodiment, the mTOR deregulation results in mTOR hyperactivity.

In one embodiment of any method, the mTOR hyperactivity is at least 10% higher compared to a control mTOR activity level. In other embodiments, the mTOR hyperactivity is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least 100% over the mTOR control. In other embodiment, the mTOR activity level is at least 2-fold, at least 5-fold, at least 10-fold, at least 100-fold, at least 1000-fold or higher as compared to the control mTOR activity level.

In one embodiment of any method described herein, the mTOR control is an mTOR activity level in a population of normal non-cancerous cells from the subject being treated. In another embodiment, the mTOR control is an average mTOR activity level in a population of healthy subjects. For example, normal non-cancer cells can be taken from the subject being treated and analyzed for cellular mTOR activity level. The normal non-cancer cells can be taken from the same organ diagnosed with cancer or tumors, or the normal non-cancer cells can be taken from other healthy organs that are free from cancer or tumors in the subject to be treated.

Alternatively, healthy cells can be collected from a population of healthy subjects, e.g., human subjects, the mTOR activity for the cells of each subject is analyzed and the average mTOR activity is calculated. The healthy cells collected from the healthy subjects can be from the same organ where cancer or tumors are diagnosed in the subject being treated. Alternatively, the healthy cells can come from a variety of tissue types in a subject.

In one embodiment of any method described, the cancer cells or tumors to be treated in the subject do not involve mTOR deregulation or hyperactivity.

In one embodiment of any method described, the cancer cells or tumors in the subject comprise a mixture of cells, some cells that involves mTOR deregulation or hyperactivity, and other cells that do do not involve mTOR deregulation or hyperactivity.

For analyzing TSC mutation and/or mTOR activity, a tissue sample is collected from the subject to be treated or healthy volunteer subjects. Cancer cells can be obtained from a subject diagnosed with or suspected of having cancer and/or tumors. For example, cancer cells can be obtained from a tissue biopsy or an excised tumor during a routine surgery to remove cancerous tumors. During the biopsy, healthy, normal non-cancer cells can be taken for analyzing the control cellular mTOR level. A skilled physician or surgeon will be able to obtain a tissue biopsy or excise a tumor from a subject. Alternatively, for TSC gene analysis, a sample of blood from the subject can be used.

In one embodiment, the tissue sample is a tumor sample. In another embodiment, the tissue sample contains cancerous cells.

As used herein, a "tissue sample" refers to a portion, piece, part, segment, or fraction of a tissue which is obtained or removed from an intact tissue of a subject, preferably a human subject. In one embodiment, the tissue sample is a blood sample. In another embodiment, the tissue sample is a bone marrow sample. In one embodiment, the tissue sample is a cerebrospinal fluid sample.

As used herein, a "tumor sample" refers to a portion, piece, part, segment, or fraction of a tumor, for example, a tumor which is obtained or removed from a subject (e.g., removed or extracted from a tissue of a subject), preferably a human subject.

In one embodiment, the tissue sample is obtained from a biopsy procedure in the subject. In another embodiment, the tissue sample is obtained from a surgical procedure to remove a tumor mass from the subject.

The cellular mTOR activity level of cancer cell and normal non-cancer cells can be analyzed by any method known in the art, for example, as described by Ikenoue T. et a., Methods Enzymol. 2009; 452:165-80; and by Jinhee Kim, et al., Methods in Molecular Biology; 2012; 821:215-225. These references are incorporated herein by reference in their entirety. Alternatively, the cellular mTOR activity level can be determined by using any one of the commercially available kits following the manufacturer's protocol, for example, the K-LISA™ mTOR Activity Kit by Merck Millipore Catalogs# CBA055 and CBA104).

For TSC loci gene analysis, the mutations in the TSC loci can be analyzed by any known genomic method in the art. For example, by single-strand conformation polymorphism analysis (SSCP) coupled with DNA sequencing as described by Galina D. et al., Am. J. Respir. Crit. Care Med.; 2001; 163:253-258; Hornigold N, et al., Oncogene; 1999; 18:2657-2661. Briefly, the coding exons of TSC1 or 2 are amplified by polymerase chain reaction (PCR) and the amplified PCR products are then analyzed for variation on DNA gels without glycerol and with 5% glycerol. As a good number of TSC loci mutations result in chain-terminating, quantitative real-time (RT-PCR) assays can be used to analyze the amount of TSC1/2 mRNA as described in Kwiatkowska J. et al., Ann Hum Genet. 1998; 62:277-85. Alternatively, commercial kits are available, e.g., $RT^2$ qPCR Primer Assay for Human TSC1 and TSC2 respectively from SABIOSCIENCES™ catalog# PPH00244B-200 and PPH00245F. The PCR primers for the human TSC1 and TSC2 can be purchased from BIORAD. Alternatively, one skilled in the art can design PCR primers for the human TSC1 and TSC2 with the following information regarding the human TSC1 and TSC2 genes:

The gene symbol, TSC1 stands for the gene name tuberous sclerosis 1. Aliases for TSC1 include; KIAA0243, LAM, MGC86987, and TSC. The RefSeqs of TSC1 are NC_000009.11; NG_012386.1; NT_035014.4. Ensembl: ENSG00000165699; Entrez: 7248; UniGene: Hs.370854.

The gene symbol, TSC2, stands for the gene name tuberous sclerosis 2. Aliases for TSC1 include FLJ43106, LAM, and TSC4. The RefSeqs of TSC2 are: NC_000016.9; NG_005895.1; NG_008412.1; NG_008617.1; and NT_010393.16. Ensembl: ENSG00000103197; Entrez: 7249; UniGene: Hs.90303.

In one embodiment of any method described, the contacted cell or the cancer to be treated involving mTOR deregulation or hyperactivity is LAM. In another embodiment, the cancer is LAM, e.g., the cancer cells tested positive for mTOR hyperactivity or increased mTOR pathway signaling.

In one embodiment of any method described, the method further comprises determining whether the cancer cells of the subject has one or more of the following features prior to administering the treatment described herein when the selected feature is present, the treatment being administering at least one COX inhibitor and/or an inhibitor of the prostaglandin biosynthesis pathway or any compositions described herein. The features being determined in the cancer cells of the subject are: (a) a mutation in the TSC locus; (b) being TSC-1 or TSC-2 deficient; (c) have overexpression of COX-1 or COX-2; (d) have lower levels of phosphos-Akt S473; (d) have higher levels of phosphos-MAPK; (e) have higher levels of phospho-S6 S235; (f) have increased production of prostaglandin; (g) insensitive to rapamycin; and (h) do not have mTOR deregulation or hyperactivity.

In one embodiment of any method described, the method further comprises selecting a subject who has cancer cells that have one or more of the following features: (a) a mutation in the TSC locus; (b) being TSC-1 or TSC-2 deficient; (c) have overexpression of COX-1 or COX-2; (d) have lower levels of phosphos-Akt S473; (d) have higher levels of phosphos-MAPK; (e) have higher levels of phospho-S6 S235; (f) have increased production of prostaglandin; (g) insensitive to rapamycin; and (h) do do not have mTOR deregulation or hyperactivity, and administering the treatment described herein when the selected feature is present, the treatment being administering at least one COX inhibitor and/or an inhibitor of the prostaglandin biosynthesis pathway or any compositions described herein.

In one embodiment of any method described, the subject is further treated with an effective amount of one or more compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, and A-77636.

In one embodiment of any method described, the subject is further treated with a therapeutically effective amount of rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil.

In one embodiment of any method described, the subject is further treated with at least one additional therapy.

In one embodiment of any method described, the at least one additional therapy is a cancer therapy.

In one embodiment of any method described, the at least one additional cancer therapy is selected from the group consisting of radiation therapy, chemotherapy, immunotherapy and gene therapy.

In one embodiment of any method described, the subject is further treated with hormone therapy. For example, progesterone, oophorectomy, tamoxifen, gonadotropin-releasing hormone (GnRH) agonists or analogues and androgen therapy.

In one embodiment of any method described, the subject is further treated with an inhibitor of the mTOR pathway, for example, rapamycin, temsirolimus, everolimus, ridaforolimus, epigallocatechin gallate (EGCG), caffeine, curcumin, resveratrol etc.

In one embodiment of any method described, the subject is human.

In one embodiment of any method described, the therapeutically effective amount of the COX inhibitor, the prostaglandin pathway inhibitor and/or the compound is administered by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and parenteral administration.

In one embodiment of any method described, the one or more inhibitor and/or additional compound used for treatment is administering by nasal inhalation such as via a nebulizer. For example, the inhibitor and/or additional compound is formulated as a powder for delivery via a nebulizer.

In one embodiment of any method described, the COX inhibitor is a COX-1 or COX-2 inhibitor. Exemplary of some COX inhibitors are the non-steroidal anti-inflammatory drugs, such as aspirin and ibuprofen.

In one embodiment of any method described, the COX inhibitor is a selective COX-1 inhibitor.

In one embodiment of any method described, the COX inhibitor is a selective COX-2 inhibitor.

In one embodiment of any method described, the COX inhibitor is selected from the group of rofecoxib, celecoxib, valdecoxib, nimesulide, ibuprofen, diclofenac, nabumetone, naprosen, aspirin and analogs thereof.

In one embodiment of any method described, the inhibitor of the prostaglandin biosynthetic pathway is indomethacin and flufenamic acid.

In one embodiment of any method described herein, a tumor in the subject being administered with the respective inhibitor or additional drug compound combinations is reduced in size by at least 10% compared to the tumor size prior to treatment with the respective drugs or drug combinations. In other embodiments, the tumor is reduced in size by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at even 100% (i.e., below detectable limits) compared to the tumor size prior to treatment with the respective inhibitor or additional drug combinations.

In one embodiment of any method described herein, the subject being treated with the respective inhibitor or additional drug compound combinations has a reduction in prostaglandin production by at least 10%. In other embodiments, the reduction in prostaglandin production is reduced by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at even 100% (i.e., below detectable limits) compared to the prostaglandin production prior to treatment with the respective inhibitor or additional drug combinations.

In one embodiment of any method described herein, the subject being treated with the respective inhibitor or additional drug compound combinations has a reduction in COX overexpression by at least 10%. In other embodiments, the reduction in COX overexpression is reduced by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at even 100% (i.e., below detectable limits) compared to the COX overexpression prior to treatment with the respective inhibitor or additional drug combinations.

In one embodiment of any method described herein, the subject being treated with the respective inhibitor or additional drug compound combinations has an improvement of lung function by at least 10%. In other embodiments, the lung function is improved by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at even 100% (i.e., below detectable limits) compared to the lung function prior to treatment with the respective inhibitor or additional drug combinations.

Contacting a Cell with a Composition as Described Herein

In one embodiment, provided herein is a method for inhibiting cell growth, the method comprising contacting a cell with an effective amount of a cyclooxygenase (COX) inhibitor or an inhibitor of the prostaglandin biosynthetic pathway. In some embodiments, the inhibition of cell growth is measured in terms of apoptosis or cell proliferation. Apoptosis or cell proliferation can be determined by any method known in the art, for example, by TUNEL DNA fragmentation assay, or by cell counting or as described in the Example.

In one embodiment of the method described, the cell has a mutation in the TSC locus. In one embodiment, the mutation is in TSC1 or TSC2. In one embodiment, the mutation is a negative mutation that results in a loss-of-function of the affected gene.

In one embodiment of the method described, the cell is TSC-1 or TSC-2 deficient.

In one embodiment of the method described, the cell has a COX overexpression. In one embodiment, the COX overexpression is a COX-1 or COX-2 overexpression.

In one embodiment of the method described, the cell has increased prostaglandin production.

In one embodiment of the method described, the cell is insensitive to rapamycin.

In one embodiment of the method described, the cell does not have mTOR deregulation or hyperactivity.

In one embodiment of the method described, the contacting period is at least one hour. In one embodiment, the contact period is at least one hour to 24 hours. In other embodiments, the contact period is at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, at least 23, or at least 24 hours. In one embodiment, the contact period is between one hour and 24 hours. In other embodiments, the contact period is two, three, four, five, six, seven, eight, nine, 10, 11, 12, 13, 14, 15, 16, 17, 18, 19, 20, 21, 22, 23, or 24 hours, including all the time periods between one to 24 hours to the minute. In other embodiments, the contacting period is between 24-72 hrs, including all the time periods between 24-72 hours to the half hour.

In one embodiment of the method described, the cell is further contacted with an effective amount of one or more compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, and A-77636.

In one embodiment of the method described, the cell is further contacted with an effective amount of of rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil.

Compositions for Treating LAM

Compositions and combinatorial compositions for the treatment of LAM are provided.

In one embodiment, provided herein is a composition comprising at least one a cyclooxygenase (COX) inhibitor or an inhibitor of the prostaglandin biosynthetic pathway for the treatment of lymphangioleiomyomatosis (LAM).

In one embodiment, provided herein is a composition comprising at least one a COX inhibitor or an inhibitor of the prostaglandin biosynthetic pathway and rapamycin for the treatment of LAM.

In one embodiment, provided herein is a composition comprising at least one a COX inhibitor or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a composition comprising at least one a COX inhibitor or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a composition comprising at least one a COX inhibitor or an inhibitor of the prostaglandin biosynthetic pathway and more than one compound (e.g., 2, 3, 4, 5, 6, 7, or more) selected from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for use treatment of LAM.

Alternatively, the compositions described herein are used for the prevention of tumor formation, reducing the frequency of tumor development, inducing apoptosis in a cell, killing a cell and inhibiting cell growth.

In some embodiments, the compositions described herein are for use in any of the methods described herein, e.g., treatment of LAM, prevention of tumor formation, reducing the frequency of tumor development, inducing apoptosis in a cell, killing a cell and inhibiting cell growth.

In another embodiment of any composition described herein, the composition is administered in conjunction with at least one additional therapy to achieve a combination therapy.

In one embodiment of any composition described herein, the composition or the combination of compounds are further administered with a pharmaceutically acceptable carrier.

In one embodiment of any composition described, the composition further comprising at least one pharmaceutically acceptable carrier.

In one embodiment of any composition described, the composition is formulated for nasal delivery such as nasal inhalation.

In one embodiment, provided herein is a use of at least one a COX inhibitor or an inhibitor of the prostaglandin biosynthetic pathway for the treatment of LAM.

In one embodiment, provided herein is a use of at least one a COX inhibitor or an inhibitor of the prostaglandin biosynthetic pathway for the manufacture of medicament for treatment of LAM.

In one embodiment, provided herein is a combinatorial use of at least one a COX inhibitor or an inhibitor of the prostaglandin biosynthetic pathway and rapamycin for the treatment of LAM.

In one embodiment, provided herein is a combinatorial use of at least one a COX inhibitor or an inhibitor of the prostaglandin biosynthetic pathway and rapamycin for the manufacture of medicament for treatment of LAM.

In one embodiment, provided herein is a combinatorial use of at least one a COXinhibitor or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a combinatorial use of at least one a COX inhibitor or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the manufacture of medicament for the treatment of LAM.

In one embodiment, provided herein is a combinatorial use of at least one a cyclooxygenase (COX) inhibitor or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the treatment of LAM.

In one embodiment, provided herein is a combinatorial use of at least one a COX inhibitor or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the manufacture of medicament for the treatment of LAM.

COX Inhibitors

The COX-2 inhibitors can include, but are in no way limited to, NS-398 (available from Cayman Chemical; Ann Arbor, Mich.), celecoxib (available from Pfizer under the trade name "CELEBREX"; New York, N.Y.), rofecoxib (available from Merck under the trade name "VIOXX"; Whitehouse Station, N.J.), valdecoxib (available from Pfizer under the trade name "BEXTRA"), meloxicam (available from Boebringer Ingelheim under the tradename "MOBICOX"; Burlington, Ontario) and pharmaceutical equivalents, derivatives and salts, as well as other functionally related compounds as will be readily appreciated by those of skill in the art. Guidance as to additional COX-2 inhibitors is provided in the literature and generally available to practitioners in the art. See, e.g., U.S. Pat. No. 6,649,645 (describing the use of radiation with COX-2 inhibitors for the treatment of cancer), which is incorporated by reference herein in its entirety.

COX-2 selective inhibitors are well understood from the patent literature. For example, compounds useful herein and methods of synthesis are disclosed U.S. Pat. No. 5,861, U.S. Pat. No. 5,859,257 and PCT WO 97/38986. These publications are incorporated by reference in their entirety. The compounds rofecoxib, MK-663, celecoxib, valdecoxib and parecoxib have known structures, as well as known dosages and dosage ranges.

Alternatively, a nonselective COX inhibitor may be used in various embodiments described herein in the form of a nonsteriodal anti-inflammatory drug (NSAID). A NSAID may include, but is in no way limited to, Retodolac, aspirin, diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, piroxicam, sunlindac, tenoxicam, tiaprofenic acid, tolmetin, and pharmaceutical equivalents, derivatives and salts, as well as other functionally related compounds, although numerous other NSAIDs may be used, as will be readily appreciated by those of skill in the art. For example, guidance as to particular NSAIDS is provided in the literature and generally available to practitioners in the art. See, e.g., U.S. Pat. No. 6,761,913 and U.S. Pat. No. 6,759,056, both of which are incorporated by reference in their entirety. In various embodiments of the present invention, the COX-2 inhibitor can be formulated in a pharmaceutical composition.

Prostaglandin Pathway Inhibitors

In the biosynthesis of prostaglandins (PG), it is known that arachidonic acid is converted firstly into $PGG_2$ by the action of cyclooxygenase, and the $PGG_2$ in turn is converted into $PGH_2$ and further to $PGD_2$, PGE2, $PHI_2$, etc. Therefore, if the first step of this cascade is inhibited, the biosynthesis of prostaglandins would be entirely inhibited. Accordingly, the term "prostaglandins" to be referred to in the phrase as "prostaglandin biosynthesis inhibitors(s)" used herein is intended to include all prostaglandins which may be biologically synthesized.

The term "prostaglandin biosynthesis inhibitors" or "prostaglandin biosynthetic pathway inhibitors" are used interchangeably and herein can include, but are in no way limited to compounds which inhibit the formation of arachidonic acid from arachidonic acid glyceride (phospholipase inhibitor) and those which inhibit the formation of prostaglandin from arachidonic acid, such as via the enzyme prostaglandin endoperoxide synthase (PGHS, aka COX-2; EC 1.14.99.1). The former includes lipomodulin (also known as macrocortin, or lipocortin), a kind of protein, and the latter includes non-steroidal anti-inflammatory substances (especially acidic ones). Specific examples of the latter are salicylic acid derivatives such as acetylsalicylic acid, salicyl salicylic acid, DL-lysine monoacetyl salicylate, etc., pyrazolone derivatives such as Phenopyrazone, Nifenazone, Phenylbutazone, Oxyphenbutazone, Ketophenylbutazone, Clofezone, Difenamizole, etc., anthranylic acid derivatives such as Mefenamic acid, Fulfenamic acid, Niflumic acid, etc., phenyl acetic acid derivatives such as Diclofenac, Ibufenac, Ibuprofen, Alclofenac, Kotoprofen, Fenbufen, Flurbiprofen, etc., indol or indazole derivatives such as Indomethacin, Sulindac, Benzydamine, etc., and further Naproxen, Tiaramide, Bucolome, Metopyrimazole, Azapropazone, etc. and their salts.

The prostaglandin biosynthetic pathway inhibitors may include, but are in no way limited to inhibitors described in U.S. Pat. Nos. 4,880,742; 5,593,994; 5,932,586; 5,973,191; 6,284,918; 8,337,914; 8,263,139; and 8,486,457, and International PCT Patent Publication Nos: WO1999/010332; WO2000/024719; and WO2006042625; these references are are incorporated by reference in their entirety.

Additional Compounds

Additional compounds that used in the methods and compositions described herein include nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucil.

It is contemplated that one or more of the disclosed compounds may be used for the treatment of LAM in combination with at least one COX inhibitor and/or with at least one inhibitor of the prostaglandin biosynthetic pathway.

Z-L-PHE chloromethyl ketone (ZPCK) is a ketone containing compound that has bioactivity in the NFAT and STAT signaling pathways. Z-L-PHE chloromethyl ketone is also known in the art as L-Carbobenzyloxyphenylalanyl chloromethyl ketone, N-Carbobenzoxy-L-phenylalanyl-chloromethyl ketone, or N-((Benzyloxy)carbonyl)-L-phenylalanine chloromethyl ketone. In one embodiment, Z-L-PHE chloromethyl ketone has the structure of Formula I.

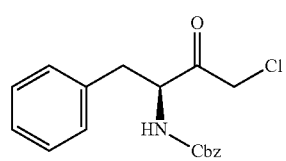

Formula I

Clemastine fumarate is an antihistamine and anticholinergic drug used for the treatment of allergy symptoms, for example, sneezing, watery eyes, itching, wheezing etc. Clemastine fumarate is also known in the art as meclastin, AGASTEN™, TAVEGIL™, and TAVEGYL™. Clemastine fumarate can be obtained commercially from e.g., NOVARTIS™ and TOCRIS BIOSCIENCE™. In one embodiment, clemastine fumarate has the structure of Formula II.

Supercinnamaldehyde is an organic compound derived from cinnamon and that gives cinnamon its flavor and color. It is used as a flavoring, a fungicide, an insecticide, an antimicrobial and an anti-cancer agent. Supercinnamaldehyde is also known in the art as 1,3-Dihydro-1-methyl-3-(2-oxopropylidene)-2H-Indol-2-one, cinnamaldehyde, trans-Cinnamaldehyde, Cinnamic aldehyde, Cinnamal, (E)-Cinnamaldehyde, 3-Phenylacrylaldehyde, Cinnamylaldehyde, Phenylacrolein, Zimtaldehyde, and Cassia aldehyde, among others. In one embodiment, supercinnamaldehyde has the structure of Formula III.

Practolol is a selective beta blocker used in the emergency treatment of cardiac arrhythmias. Practolol is also known in the art as ERALDIN™, DALZIC™, PRAKTOL™, CARDIOL™, PRALON™, CORDIALINA™, ERALDINA™, and TERANO™. In one embodiment, practolol has the formula of Formula IV.

Fluvastatin (fluvastatin Na or fluvastatin sodium) is a member of the statin family of compounds used for the treatment of hypercholesterolemia and the prevention of heart disease. Fluvastatin is also known in the art as LESCOL™, CANEF™, and VASTIN™. In one embodiment, fluvasatin has the formula of Formula V.

Sulindac is a Non-Steroidal Anti-Inflammatory Drug (NSAID) used for the treatment of pain and inflammatory conditions, such as rheumatoid arthritis, osteoarthritis, gout, dysmenorrhea, metastatic bone pain, fever, headache, muscle stiffness and migraine, among others. Sulindac can be obtained from MERCK™ under the name CLINORIL™. In one embodiment, sulindac has the formula of Formula VI.

Amorolfine is a morpholine antifungal drug that is used primarily to treat fungal infections in toenails and fingernails. Amorolfine is also known as CURANAIL™ LOCERYL™, LOCETAR™, and ODENIL™. In one embodiment, amorolfine has the formula of Formula VII.

Spectinomycin is an antibiotic closely related to the aminoglycoside antibiotics. Spectinomycin has been used as an injected antibiotic for the treatment of gonorrhea. Spectinomycin is also known in the art as TROBICIN™. In one embodiment, spectinomycin has the formula of Formula VIII.

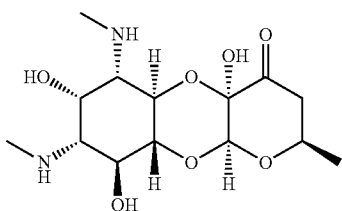

Formula VIII

Sibutramine HCL or sibutramine is an oral anorexient used for the treatment of obesity in conjunction with diet and exercise. Sibutramine is also known in the art as REDUCTIL™, MERIDIA™ and SIBUTREX™. In one embodiment, sibutramine has the formula of Formula IX.

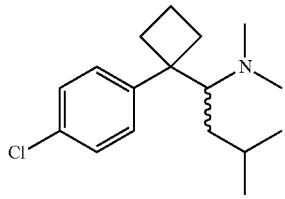

Formula IX

Nelfinavir mesylate is a protease inhibitor and antiretrovirall drug useful for treating HIV infection. Nelfinavir is also known in the art as VIRACEPT™. In one embodiment, nelfinavir has the formula of Formula X.

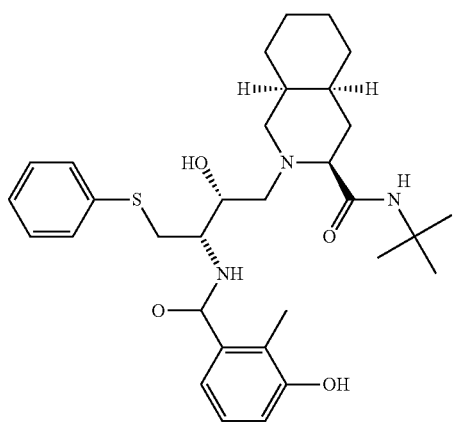

Formula X

Moroxydine HCL or moroxydine is a heterocyclic biguanidine antiviral drug useful for the treatment of influenza. Moroxydine is also known by the following chemical synonyms: ABOB, VIRONIL™, moroxydine; moroxydinum, TIMTEC-BB, SBB003847, 1-(1-morpholinoformimidoyl) guanidine, n-(aminoiminomethyl)-4-morpholinecarboximidamide; 4-morpholinecarboximidamide, and N-(aminoiminomethyl)-; N-[amino(imino)methyl]morpholine-4-carboximidamide hydrochloride. In one embodiment, moroxydine has the formula of Formula XI.

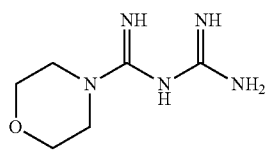

Formula XI

Nicotine ditartrate is a nicotine derivative that exhibits vasoconstrictive, hypertensive and prothrombotic activity. Nicotine ditartrate is also known by the following chemical synonyms: nicotine tartrate, tartratedenicotine, nicotine bitartrate, nicotine acid tartrate, nicotine, tartrate(1:2), (−)-Nicotine dirartate, and nicotinehydrogentartrate. In one embodiment, nicotine ditartrate has the formula of Formula XII.

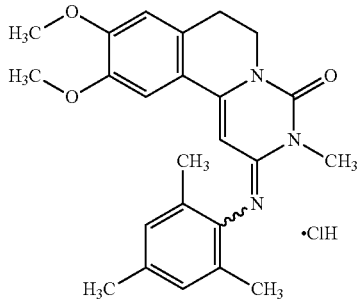

Formula XII

Trequinsin (also known as 9,10-Dimethoxy-2-mesityl-imino-3-methyl-2,3,6,7-tetrahydro-4H-pyrimido-[6,1a]-isoquinolin-4-one) is a cGMP-inhibited phosphodiesterase III inhibitor useful in the treatment of short term cardiac failure and intermittent claudication. In one embodiment, trequinsin has the formula of Formula XIII.

Formula XIII

Meglumine is a sugar derived from sorbitol and is typically used as an excipient in pharmaceutical compositions or with iodinated organic compounds as a contrast medium. Meglumine is also known in the art as: N-Methyl-D-glucamine, Meglumin, N-Methylglucamine, 6284-40-8, 1-Deoxy-1-methylaminosorbitol, Megluminum, Methylglucamin, Meglumina, and 1-Deoxy-1-(methylamino)-D-glucitol. In one embodiment, meglumine has the formula of Formula XIV.

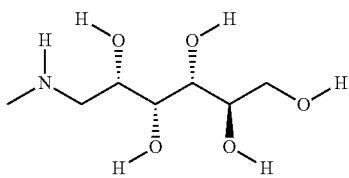

Formula XIV

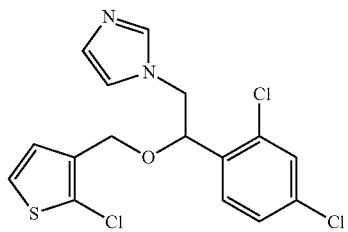

Formula XVII

Tizanidine HCl or tizanidine is used as a muscle relaxant in the treatment of a variety of conditions including, but not limited to, spasms, cramping, and tightness of muscles caused by medical problems such as multiple sclerosis, spastic diplegia, back pain, or injuries to the spine or central nervous system. Tizanidine is also known in the art as ZANAFLEX™, and SIRDALUD™. In one embodiment, tizanidine has the formula of Formula XV.

TOVOK™ (afatinib) is a next generation tyrosine kinase inhibitor and an anti-cancer compound that may be useful in the treatment of non-small cell lung carcinoma, breast cancer, prostate cancer, glioma, and head and neck cancer. TOVOK™ is also known in the art as TOMTOVOK™ and can be obtained commercially from BOEHRINGER INGELHEIM™. In one embodiment, TOVOK™ has the formula of Formula XVIII.

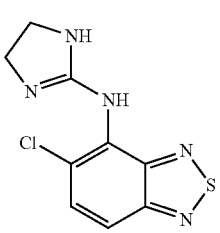

Formula XV

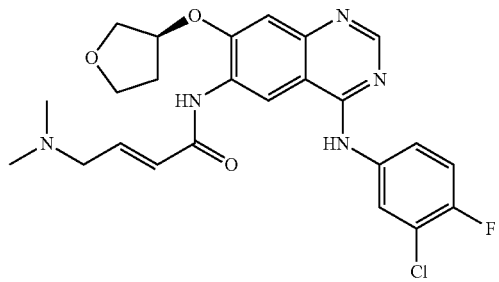

Formula XVIII

CGP-74514A hydrochloride is also known in the art by the following chemical synonyms: compound 13 hydrochloride, and N2-(CIS-2-AMINOCYCLOHEXYL)-N6-(3-CHLOROPHENYL)-9-ETHYL-9H-PURINE-2,6-DIAMINE HYDROCHLORIDE. In one embodiment, CGP-74514A hydrochloride has the formula of Formula XVI.

Kasugamycin is an aminoglycoside antibiotic also known as kasumin, 3-O[2-Amino-4-[(carboxyiminomethyl)amino]-2,3,4,6-tetradeoxy-D-arabino-hexopyranosyl]-D-chiro-inositol, and 2-amino-2-[(2R,3 S,5 S,6R)-5-amino-2-methyl-6-[(2R,3 S,5 S,6 S)-2,3,4,5,6-pentahydroxycyclohexyl]oxyoxan-3-yl]iminoacetic acid. In one embodiment, kasugamycin has the formula of Formula XIX.

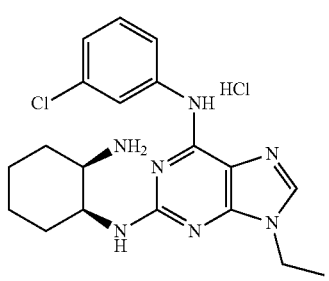

Formula XVI

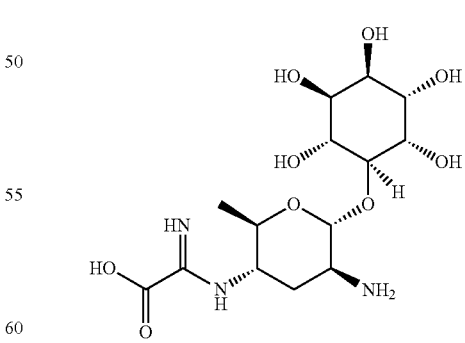

Formula XIX

Tioconazole is an antifungal compound useful for treating vaginal yeast infections, ringworm, jock itch, athlete's foot, and tinea versicolor. Tioconazole is also known in the art as TROSYD™, and GYNO-TROSYD™, both of which can be obtained commercially from PFIZER™. In one embodiment, tioconazole has the formula of Formula XVII.

Nateglinide is a meglitinide compound used for reducing blood glucose levels in the treatment of Type II diabetes. Nateglinide is also known in the art as STARLIX™ and can be obtained commercially from NOVARTIS™. In one embodiment, nateglinide has the structure of Formula XX.

Formula XX

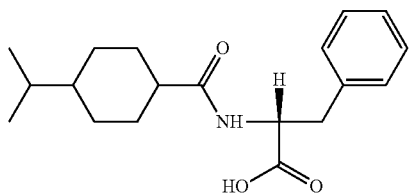

Methods for synthesizing the foregoing compounds are known in the art. Moreover, the foregoing compounds are commercially available, e.g. clemastine fumarate is available from NOVARTIS™ as MECLASTIN™.

It is also contemplated that the methods described herein can be used as prophylaxis. Since subjects with TSC are prone to developing tumors in various organs, administration of the inhibitors or compositions can help prevent tumor formation and thereby reduce the frequency of these tumors in such individuals.

A skilled physician will be able to diagnose LAM and/or LAM/TSC, for example-, based on known clinical symptoms, lung tissue biopsy and genetic analysis of the TSC loci in the afflicted subject.

In one embodiment, provided herein is a composition comprising at least one COX inhibitor and/or a prostaglandin biosynthesis pathway inhibitor and at least one compound (e.g., 2, 3, 4, 5, 6, 7, or more) selected from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucil for use in any of the methods described herein, e.g., treatment of LAM and/or LAM/TSC, prevention of tumor formation, reducing the frequency of tumor development, inducing apoptosis in a cell, killing a cell and inhibiting cell growth.

In one embodiment, the method for treating LAM in a subject comprises administering to a subject in need thereof a therapeutically effective amount of any one of the composition described herein. For example, a composition comprising at least one COX inhibitor and/or a prostaglandin biosynthesis pathway inhibitor and at least compound selected from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), and kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucil.

In one embodiment, provided herein is a method for treating LAM in a subject, the method comprising determining whether the cancer cells of the subject or the subject comprises one or more of the following: (a) a COX overexpression; (b) a mutation in the TSC locus; (c) increased prostaglandin production; (d) absence of mTOR deregulation or hyperactivity ie., normal mTOR regulation or activity; and (e) at least one cancer cell that is insensitive to rapamycin; and if any is affirmative or positive, administering to the subject a therapeutically effective amount of a composition comprising at least one of the composition described herein. For example, a composition comprising at least one COX inhibitor and/or a prostaglandin biosynthesis pathway inhibitor and at least compound selected from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucil. For example, a composition comprising at least one COX inhibitor and/or a prostaglandin biosynthesis pathway inhibitor and rapamycing and at least and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil.

In some embodiments, a combination of more than one compositions described herein can be administered for the treatment of LAM. In one embodiment relating to combination therapy with more than one compositions, the compositions are administered together, e.g., in a cocktail, admixture or as a single pharmaceutical composition.

In one embodiment of any method or composition described herein, the COX inhibitors, the prostaglandin biosynthesis pathway inhibitors and compound(s) are administered by a route selected from the group consisting of aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor and parenteral route.

In one embodiment of any method or composition described, only one compound selected from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucil are administered. In other embodiments, at least two compounds, at least three compounds, or more compounds selected from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucilare administered. For example, only practolol and fluvastatin Na are administered. All possible two compound combinations derived from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and Chlorambucil are contemplated herein for use as a combination therapy. All possible three compound combinations derived from the group consisting of nateglinide, Z-L-Phe chloroethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-7451A hydrochloride, tioconazole, TOVOK™ (afatinib), kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, Kanamycin, SCH-202676 hydrobromide, danusertib (PHA-739358), AZ-960, nicardipine, SB-590885, Thimerosal, ionomycin, U-73343, PAF C16, BX912, and chlorambucil are contemplated herein for use as a combination therapy.

In one embodiment of any method or composition described herein, the COX inhibitor and/or a prostaglandin biosynthesis pathway inhibitor or composition is administered in conjunction with at least one additional therapy to achieve a combination therapy.

In one embodiment of any method or composition described herein, the COX inhibitor and/or a prostaglandin biosynthesis pathway inhibitor or composition is further administered with a pharmaceutically acceptable carrier.

In one embodiment of any method or composition described, the at least one additional therapy is a therapy that help the subject cope with cancer treatment side effects. For example, aromatherapy, exercise, hypnosis, massage, meditation, tai chi, yoga, acupuncture, music therapy and relaxation techniques.

In one embodiment of any method or composition described herein, the at least one additional cancer therapy is selected from therapies such as one or more anti-cancer therapeutic agents selected from the group consisting of growth inhibitory agents, cytotoxic agents, anti-angiogenesis agents, apoptotic agents, anti-tubulin agents, anti-HER-2 antibodies, anti-CD20 antibodies, an epidermal growth factor receptor (EGFR) antagonist, a HER1/EGFR inhibitor, a platelet derived growth factor inhibitor, a COX-2 inhibitor, an interferon, and a cytokine (e.g., G-C SF, granulocyte-colony stimulating factor).

In one embodiment of any method or composition described, the at least one additional therapy is a cancer therapy. Non-limiting examples of anti-cancer therapeutic agents are 13-cis-retinoic acid, 2-CdA, 2-Chlorodeoxyadenosine, 5-Azacitidine, azacytidine, 5-Fluorouracil, 5-FU, 6-Mercaptopurine, 6-MP, 6-TG, 6-Thioguanine, abiraterone acetate, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Cabazitaxel, Calcium Leucovorin, Campath® Camptosar® Camptothecin-11, Capecitabine, Caprelsa® Carac™ Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Crizotinib, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, Denosumab, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eculizumab, Efudex®, Eligard™, Ellence™, Eloxatin™, Elspar®, Emcyt®, Epirubicin, Epoetin Alpha, Erbitux, Eribulin, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, Gefitinib, Gemcitabine, Gemtuzumab ozogamicin, Gemzar, Gleevec™, Gliadel® Wafer, Goserelin, Granulocyte-Colony Stimulating Factor (G-CSF), Granulocyte Macrophage Colony Stimulating Factor (GM-CSF), Halaven®, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Inlyta®, Interferon alpha, Interferon Alpha-2b (PEG Conjugate), Interleukin-2, Interleukin-11, Intron A® (interferon alpha-2b), Ipilimumab, Iressa®, Irinotecan, Isotretinoin, Ixabepilone, Ixempra™, Jevtana®, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolia®, Prolifeprospan 20 with Carmustine Implant, Provenge®, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Sipuleucel-T, Soliris®, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, Valrubicin, Valstar, vandetanib, VCR, Vectibix™, Velban®, Velcade®, Vemurafenib, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xalkori capsules, Xeloda®, Xgeva®, Yervoy®, Zanosar®, Zelboraf, Zevalin™, Zinecard®, Zoladex®, Zoledronic acid, Zolinza, Zometa®, and Zytiga®.

In one embodiment of any method or composition described herein, the at least one additional cancer therapy is selected from the group consisting of radiation therapy, chemotherapy, immunotherapy and gene therapy.

In one embodiment of any method described herein, the method further comprises administering a drug that treats at least one symptom of cancer or cancer therapy. For example, for low blood count or anemia resulting from the chemo- or radiation therapy, erythropoietin can be administered to promote de novo the production of blood cells.

In one embodiment of any method described, each compound is administered singly, i.e. each compound is administered independently of the others. In another embodiment of any method described, the compounds are administered singly and simultaneously. In another embodiment, the compounds are administered together, e.g., in a cocktail or a pharmaceutical composition.

In one embodiment of any composition described, the composition is formulated for administration by a route selected from the group consisting of: aerosol, direct injection, local, systemic, intradermal, direct inhalation, intranasal, intravenous, intravitreal, intramuscular, subcutaneous, intradermal, transdermal, topical, oral, intraperitoneal, intrathecal, intrapleural, intrauterine, transmucosal, buccal, rectal, epidural, vaginal, intrasynovial, intraocular/periocular, intraorgan, intratumor, and parenteral administration.

In one embodiment of any method described herein, the method further comprises selecting a subject who has LAM or has been diagnosed with LAM. The subject can be further diagnosed with a mutation in the TSC locus. The subject can be screened for LAM with a combination with diagnostics such as, for example, additional biomarkers, mammography, manual examination, MM, or tissue biopsy and histopathological examination. A skilled oncologist or physician will be able to differentially diagnose cancer using medical diagnostic methods known within the art.

Formulation and Application

In one embodiment, the compounds or combination of compounds are delivered with a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

Therapeutic compositions contain a physiologically tolerable carrier together with at least a compound or combination of compounds as described herein, dissolved or dispersed therein as an active ingredient. In one embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Compositions can be prepared as injectable either as liquid solutions or suspensions, however, solid forms suitable for solution, or suspensions; in liquid prior to use can also be prepared. The preparation can also be emulsified or presented as a liposome composition. The compounds or combination of compounds can also be conjugated with lipids, e.g., amphipathic lipids, for stability and delivery purposes. The conjugation bonds are reversible and are broken or dissolved when the compounds or combination of compounds are delivered to target destination. Alternatively, the compounds or combination of compounds described herein can be prepared as a solid or semi-solid or emulsion in suppository, e.g., as microspheres. The microspheres can be inserted as a solid into or targeted to a solid tumor. The compounds or combination of compounds described herein can be mixed with excipients which are pharmaceutically acceptable and compatible with the active ingredient and in amounts suitable for use in the therapeutic methods described herein. Specifically contemplated pharmaceutical compositions are compounds or combination of compounds in a preparation for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition comprising the compounds or combination of compounds described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of compounds or combination of compounds or composition used in the methods described herein that will be effective in the treatment of a particular disorder or condition will depend on the nature of the disorder or condition, and can be determined by standard clinical techniques.

The therapeutic compositions or pharmaceutical compositions described herein can be formulated for passage through the blood-brain barrier or direct contact with the endothelium. In some embodiments, the compositions can be formulated for systemic delivery. In some embodiments, the compositions can be formulated for delivery to specific organs, for example but not limited to the liver, spleen, the bone marrow, and the skin. The compositions or pharmaceutical compositions can also be formulated for aerosol application by inhalation into the lung. Alternatively, the therapeutic compositions or pharmaceutical compositions can also be formulated for a transdermal delivery, e. g. via a skin patch. Therapeutic compositions or pharmaceutical compositions can be enteric coated and formulated for oral delivery. Alternatively, the compositions or pharmaceutical compositions can be encapsulated in liposomes or nanoparticles and formulated for slow sustained delivery in vivo. Alternatively, the therapeutic compositions or pharmaceutical compositions is be formulated for targeted delivery, eg., encapsulated in liposomes or nanoparticles that are designed and feature targeting moiety to on the liposomes or nanoparticles.

The therapeutic compositions or pharmaceutical compositions described herein can be administered by any known route. By way of example, the therapeutic compositions or pharmaceutical compositions described herein can be administered by a mucosal, pulmonary, topical, or other localized or systemic route (e.g., enteral and parenteral). The compositions may be administered by any convenient route, for example by infusion or bolus injection, by absorption through epithelial or mucocutaneous linings (e.g., oral mucosa, rectal and intestinal mucosa, etc.) and may be administered together with other active agents.

Routes of administration include, but are not limited to aerosol, direct injection, intradermal, transdermal (e.g., in slow release polymers), intravitreal, intramuscular, intraperitoneal, intravenous, subcutaneous, epidural, topical, oral, transmucosal, buccal, rectal, vaginal, transdermal, intranasal and parenteral routes.

"Parenteral" refers to a route of administration that is generally associated with injection, including but not limited to intraorbital/periocular, infusion, intraarterial, intracapsular, intraocular, intracardiac, intraorgan, intradermal, intrahepatic, intrarogan, intramuscular, intraperitoneal, intrapulmonary, intratumor, intraspinal, intrasternal, intrathecal, intrauterine, intravenous, subarachnoid, subcapsular, intrasynovial, subcutaneous, transmucosal, or transtracheal. Any other therapeutically efficacious route of administration can be used, for example, infusion or bolus injection, absorption through epithelial or mucocutaneous linings. In various embodiments, administration can be inhaled in to the lung via aerosol administration, e.g. with nebulization. Administration also can be systemic or local, for example, intratumoral delivery is also included.

In some embodiments, the one or more compounds used for treatment or the therapeutic compositions or pharmaceutical compositions described herein are administering via a nebulizer. For example, the agent can be formulated as a powder for delivery via a nebulizer.

For example, the one or more compounds used for treatment or the therapeutic compositions or pharmaceutical compositions described herein are formulated for delivery by nebulizer. Such formulations are known in the art. For examples, nebulizer formulations are described in O'Riordan T G. et al., 2002, Respir Care. 47:1305-12; U.S. Patent publication US20070207091; and U.S. Pat. No. 7,405,207; the contents of which are incorporated by reference in their entirety. Other dary inhalation formulation are known in the art, for example, in U.S. Pat. Nos. 5,983,956, 6,027,714, and 8,071,127, and U.S. Patent publication US2003/0148925 and US2011/0236492, the contents of which are incorporated by reference in their entirety.

The precise dose and formulation to be employed depends upon the potency of the compounds or combination of compounds described herein, and depends on the amounts large enough to produce the desired effect, e.g., a reduction in size and/or growth of the tumors in the subject. The dosage should not be so large as to cause unacceptable adverse side effects. Generally, the dosage will vary with the compounds or combination of compounds, and with the age, condition, and size of the tumors in the subject are also considered. Dosage and formulation of the compounds or combination of compounds will also depend on the route of administration, and the mass and number of tumors in the subject, and should be decided according to the judgment of the practitioner and each subject's circumstances. Effective doses can be extrapolated from dose-response curves derived from in vitro or animal model test systems.

The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 g/kg body weight to 30 g/kg body weight. Alternatively, the dose range will be titrated to maintain serum levels between 5 g/mL and 30 g/mL.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy, e.g., shrinkage of tumor sizes. Continuous, relatively low maintenance doses are contemplated after an initial higher therapeutic dose. As but one example, the compounds or combination of compounds and a pharmaceutically acceptable carrier can be formulated for direct application by injection into the tumor in the subject.

Efficacy testing can be performed during the course of treatment using the methods described herein, e.g., ultrasound, MRI and CT to monitor the shrinkage in size of the tumors in the treated subject. A decrease in size of the tumors during and after treatment indicates that the treatment is effective in reducing tumor size. Measurements of the degree of severity of a number of symptoms associated with cancerous tumors are also noted prior to the start of a treatment and then at later specific time period(s) after the start of the treatment. A skilled physician will be able to ascertain the tumor sizes and related symptoms by known methods in the art and those described herein.

Those skilled in the art will recognize, or be able to ascertain using not more than routine experimentation, many equivalents to the specific embodiments of the disclosure described herein. Such equivalents are intended to be encompassed by the following claims.

The references cited herein and throughout the specification are incorporated herein by reference.

Some embodiments of the technology described herein can be defined according to any of the following numbered paragraphs:

[1] A composition comprising at least one a cyclooxygenase (COX) inhibitor and/or an inhibitor of the prostaglandin biosynthetic pathway for the treatment of lymphangioleiomyomatosis (LAM).

[2] A composition comprising at least one a cyclooxygenase (COX) inhibitor and/or an inhibitor of the prostaglandin biosynthetic pathway and rapamycin.

[3] A composition comprising at least one a cyclooxygenase (COX) inhibitor and/or an inhibitor of the prostaglandin biosynthetic pathway and rapamycin for the treatment of lymphangioleiomyomatosis (LAM).

[4] A composition comprising at least one a cyclooxygenase (COX) inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil.

[5] A composition comprising at least one a cyclooxygenase (COX) inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the treatment of lymphangioleiomyomatosis (LAM).

[6] A composition comprising at least one a cyclooxygenase (COX) inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the treatment of lymphangioleiomyomatosis (LAM).

[7] A composition comprising at least one a cyclooxygenase (COX) inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil.

[8] The composition of any one of claims 1-7, further comprising at least one pharmaceutically acceptable carrier.

[9] Use of at least one a cyclooxygenase (COX) inhibitor and/or at least one inhibitor of the prostaglandin biosynthetic pathway for the treatment of lymphangioleiomyomatosis (LAM).

[10] Use of at least one a cyclooxygenase (COX) inhibitor and/or at least one inhibitor of the prostaglandin biosynthetic pathway for the manufacture of medicament for treatment of lymphangioleiomyomatosis (LAM).

[11] A combinatorial use of at least one a cyclooxygenase (COX) inhibitor and/or at least one inhibitor of the prostaglandin biosynthetic pathway and rapamycin for the treatment of lymphangioleiomyomatosis (LAM).

[12] A combinatorial use of at least one a cyclooxygenase (COX) inhibitor and/or at least one inhibitor of the prostaglandin biosynthetic pathway and rapamycin for the manufacture of medicament for treatment of lymphangioleiomyomatosis (LAM).

[13] A combinatorial use of at least one a cyclooxygenase (COX) inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the treatment of lymphangioleiomyomatosis (LAM).

[14] A combinatorial use of at least one a cyclooxygenase (COX) inhibitor and/or an inhibitor of the prostaglandin biosynthetic pathway, rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil for the manufacture of medicament for the treatment of lymphangioleiomyomatosis (LAM).

[15] A combinatorial use of at least one a cyclooxygenase (COX) inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the treatment of lymphangioleiomyomatosis (LAM).

[16] A combinatorial use of at least one a cyclooxygenase (COX) inhibitor and/or an inhibitor of the prostaglandin biosynthetic pathway and at least one compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil for the manufacture of medicament for the treatment of lymphangioleiomyomatosis (LAM).

[17] A method for treating lymphangioleiomyomatosis (LAM) in a subject in need comprising administering to a subject therapeutically effective amount of a composition in any one of paragraphs 1-7.

[18] A method for treating lymphangioleiomyomatosis (LAM) in a subject in need comprising administering to a subject therapeutically effective amount of a cyclooxygenase (COX) inhibitor or an inhibitor of the prostaglandin biosynthetic pathway.

[19] The method of claim 1, wherein the subject has a negative mutation in the tuberous sclerosis complex (TSC) gene 1 or 2.

[20] The method of paragraph 17, 18 or 19, wherein the cancer cells of the subject have a mutation in the TSC locus.

[21] The method of paragraph 20, wherein the cancer cells of the subject are TSC-1 or TSC-2 deficient.

[22] The method of any one of paragraphs 17-21, wherein the subject has COX-1 or COX-2 overexpression.

[23] The method of any one of paragraphs 17-22, wherein the subject has an increased prostaglandin production.

[24] The method of any one of paragraphs 17-23, wherein at least one cancer cell of the subject is insensitive to rapamycin.

[25] The method of any one of paragraphs 17-24, wherein at least one cancer cell of the subject does not involve mTOR deregulation or hyperactivity.

[26] The method of any one of paragraphs 17-25, further comprising determining whether the subject has a negative mutation in the tuberous sclerosis complex (TSC) gene 1 or 2.

[27] The method of any one of paragraphs 17-26, further comprising selecting the subject having a negative mutation in the tuberous sclerosis complex (TSC) gene 1 or 2.

[28] The method of any one of paragraphs 17-9, further comprising determining whether the cancer cells of the subject are TSC-1 or TSC-2 deficient.

[29] The method of any one of paragraphs 17-28, further comprising selecting the subject having cancer cells that are TSC-1 or TSC-2 deficient.

[30] The method of any one of paragraphs 17-29, further comprising selecting the subject having COX-1 or COX-2 overexpression.

[31] The method of any one of paragraphs 17-30, further comprising selecting the subject having increased prostaglandin production.

[32] The method of any one of paragraphs 17-31, wherein the subject is further treated with an effective amount of one or more compounds selected from the group consisting of nateglinide, Z-L-Phe chloromethyl ketone, clemastine fumarate, supercinnamaldehyde, practolol, fluvastatin Na, sulindac, 6-bromoindirubin-3'-oxime (BIO), amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, betaxolol hydrochloride, salmeterol, chelerythrine chloride, paroxetine, trifluoperazine, fluoxetine, methiothepin, nortriptyline, and A-77636.

[33] The method of any one of paragraphs 17-32, wherein the subject is further treated with a therapeutically effective amount of rapamycin and at least one compound selected from the group consisting of SCH-202676 hydrobromide, danusertib (PHA-739358), AZ-960, nicardipine, SB-590885, Thimerosal, ionomycin, U-73343, PAF C16, BX912, and Chlorambucil.

[34] The method of any one of paragraphs 17-33, wherein the subject is further treated with at least one additional therapy.

[35] The method of any one of paragraphs 17-34, wherein the at least one additional therapy is a cancer therapy.

[36] The method of paragraph 35, wherein the at least one additional cancer therapy is selected from the group consisting of radiation therapy, chemotherapy, immunotherapy and gene therapy.

[37] The method of any one of paragraphs 17-36, wherein the subject is further treated with hormone therapy.

[38] The method of any one of paragraphs 17-37, wherein the subject is human.

[39] The method of any one of paragraphs 17-38, wherein the therapeutically effective amount of the inhibitor and/or compound is administered by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and parenteral administration.

[40] The method of any one of paragraphs 17-39, wherein the COX inhibitor is a COX-1 or COX-2 inhibitor.

[41] The method of paragraph 40, wherein the COX inhibitor is selected from the group of rofecoxib, celecoxib, valdecoxib, nimesulide, ibuprofen, diclofenac, nabumetone, naprosen, aspirin and analogs thereof.

[42] The method of any one of paragraphs 17-41, wherein the inhibitor of the prostaglandin biosynthetic pathway is indomethacin or flufenamic acid.

[43] A method for treating lymphangioleiomyomatosis (LAM) in a subject in need comprising (a) determining whether the subject has a mutation in the tuberous sclerosis complex (TSC) locus and (b) administering to the subject therapeutically effective amount of a composition in any one of paragraphs 1-7 when the subject is determined to have a TSC mutation.

[44] A method for treating lymphangioleiomyomatosis (LAM) in a subject in need comprising (a) selecting a subject having COX-1 or COX-2 overexpression; and (b) administering to the subject therapeutically effective amount of a composition in any one of paragraphs 1-7.

[45] A method for treating lymphangioleiomyomatosis (LAM) in a subject in need comprising (a) selecting a subject having increased prostaglandin production; and (b) administering to a subject therapeutically effective amount of a composition in any one of paragraphs 1-7.

[46] A method for treating lymphangioleiomyomatosis (LAM) in a subject in need comprising (a) selecting the subject having a negative mutation in the tuberous sclerosis complex (TSC) locus and (b) administering to a subject therapeutically effective amount of a composition in any one of paragraphs 1-7.

[47] A method for treating lymphangioleiomyomatosis (LAM) in a subject in need comprising (a) selecting a subject who has at least one cancer cell that is insensitive to rapamycin; and (b) administering to a subject therapeutically effective amount of a composition in any one of paragraphs 1-7.

[48] A method for treating lymphangioleiomyomatosis (LAM) in a subject in need comprising (a) selecting a subject who has at least one cancer cell that does not have mTOR deregulation or hyperactivity; and (b) administering to a subject therapeutically effective amount of a composition in any one of paragraphs 1-7.

This disclosure is further illustrated by the following example which should not be construed as limiting. The contents of all references cited throughout this application, as well as the figures and table are incorporated herein by reference.

EXAMPLE

Lymphangioleiomyomatosis (LAM) is a female predominant interstitial lung disease due to proliferating smooth muscle-like (LAM) cells that typically have TSC2 mutation, leading to mTORC1-activation (1-5). mTORC1 regulates cell growth, protein translation and metabolism (6). In a randomized clinical trial the mTORC1 inhibitor rapamycin stabilized lung function and improved symptoms in LAM patients. However, lung function declined when rapamycin was discontinued (7). The female predominance of LAM, coupled with the genetic evidence indicating that estrogen promotes the metastasis of cells with mTORC1 activation (1,4). It was previously have discovered that estrogen increases levels of circulating tumor cells and pulmonary metastases of tuberin-deficient cells in a xenograft model of LAM (8). Studies have demonstrated that estrogen induces COX-2-mediated prostaglandin synthesis (9). COX-2 is a rate-limiting enzyme catalyzing the conversion of arachidonate to prostaglandins. COX-2 overexpression has been documented in human tumors, and prostaglandins may contribute to cancer development (10-13). In this study, it was discovered that estrogen enhances prostaglandin production in TSC2-deficient cells. Surprisingly, loss of TSC2 increases COX-2 and prostaglandin biosynthesis in a rapamycin-insensitive manner, indicating an mTORC1-independent pathway. Aspirin suppresses tumor progression in a xenograft tumor model. This study indicates that targeting COX-2 with aspirin or related drugs may have therapeutic benefit in LAM and TSC-related diseases.

Methods

Cell culture and reagents. ELT-3 cells (Eker rat uterine leiomyoma-derived) (22,23) and LAM patient-derived 621-101 cells were cultured in IIA complete medium. HeLa, U2OS and OVARC5 cells were cultured in DMEM supplemented with 10% FBS. 17-beta-estradiol (10 nM), rapamycin (20 nM, Biomols), NS398 (50 µM), aspirin (450 µM Sigma), and 15-epi-LXA4 (100 nM) were used as indicated.

Animal studies. All animal work was performed in accordance with protocols approved by the IACUC-BWH. Female intact CB17-SCID mice were used as described previously (8, 24, 25). Aspirin (100 mg/kg/day, in drinking water) treatment was initiated five weeks post-cell inoculation. Urine specimens were collected.

Quantitative RT-PCR. RNA from cultured cells and xenograft tumors was isolated using RNeasy Mini Kit (QIAGEN). Gene expression was quantified using One-Step qRT-PCR Kits (INVITROGEN) in the Applied Biosystems Real-Time PCR System and normalized to beta-actin.

Immunoblotting and antibodies. Cells were lysed in m-PER buffer (PIERCE). Antibodies were used: COX-1, COX-2, phospho-MAPK (T202/Y204), phospho-S6 (S235/236), Cleaved caspase 3, cleaved PARP (CELL SIGNALING), tuberin and c-Myc (SANTA CRUZ), smooth muscle actin (BIOGENEX), and beta-actin (SIGMA).

Immunohistochemistry. Sections were deparaffinized, incubated with primary antibodies and biotinylated secondary antibodies and counterstained with Gill's Hematoxylin.

Quantification of prostaglandin levels. PGE2, 6-keto-PGF1α and creatinine were measured using enzyme immunoassay kits (Cayman Chemical). Levels of secreted prostaglandins were normalized to protein concentrations and expressed as pg/mg protein. Urinary levels of prostaglandins were normalized to creatinine levels and expressed as ng/mL.

Statistical analyses. Statistical analyses were performed using Student's t-test when comparing two groups for in vitro and in vivo studies. Two-Way ANOVO test was performed in xenograft tumor-aspirin studies. Mann Whitney tests were used for prostaglandin quantification in clinical data.

Metabolomic profiling. 100 µg of frozen biopsy tissue was submitted to Metabolon, Inc. (Durham, N.C.) for sample extraction and analysis. In brief, Metabolon performed cold methanol extraction of mechanically disaggregated tissue samples and these extracts were split into three aliquots. The reproducibility of the extraction protocol was assessed by the recovery of xenobiotic compounds spiked into every tissue sample prior to extraction. These aliquots were processed and characterized by one of the three analytical methods previously described: UHPLC-ESI-MS/MS in the positive ion mode, UHPLC-ESI-MS/MS in the negative ion mode and sialylation followed by GC-EI-MS. Chromatographic timelines were standardized using a series of xenobiotics that elute at specified intervals throughout each chromatographic run. The technical variability of each analytical platform was assessed by repeated characterization of a pooled standard that contained an aliquot of each sample within the study.

Results

Identification of an Estrogen-Induced Prostaglandin Biosynthesis Signature in TSC2-Deficient Cells and Xenograft Tumors To examine the possible effects of estrogen on metabolic pathways in Tsc2-deficient rat-uterus-derived ELT3 cells 14, a metabolomic screen was performed. A significant increase in prostaglandins including PGE2, PGD2, and 6-keto-PGF1α, was seen in estrogen-treated cells (FIGS. 1a and 1b). Furthermore, estrogen increased MAPK phosphorylation, COX-2 expression, and PGE2 levels in TSC2-deficient cells at 2 and 24 hr (FIGS. 1c and 1d). Analysis of LAM patient-derived TSC2-deficient 621-101 cells showed that estrogen also increased COX-2 expression (FIG. 1e) and PGE2 levels at 24 hr (FIG. 1f), confirming the results in the Tsc2-deficient ELT3 cells.

To determine the effect of estrogen on cellular metabolomics in vivo, xenograft tumors of Tsc2-deficient ELT3 cells (8) from placebo or estrogen-implanted ovariectomized female mice were used. MAPK phosphorylation was evident in xenograft tumors from estrogen-treated mice (Data not shown). The metabolomic screen showed that PGE2 and PGD2 levels were significantly increased in xenograft tumors from mice treated with estrogen (FIGS. 1g and 1i). Estrogen-treated mice bearing ELT3 xenograft tumors also exhibited higher levels of urinary PGE2 and PGD2 relative to placebo controls (FIG. 1j). These data demonstrate that estrogen stimulates prostaglandin biosynthesis by TSC2-deficient cells in vitro and in vivo.

TSC2 Negatively Regulates COX-2 Expression and Prostaglandin Production in Rapamycin-Insensitive Manner In Vitro and In Vivo.

Figure 8:
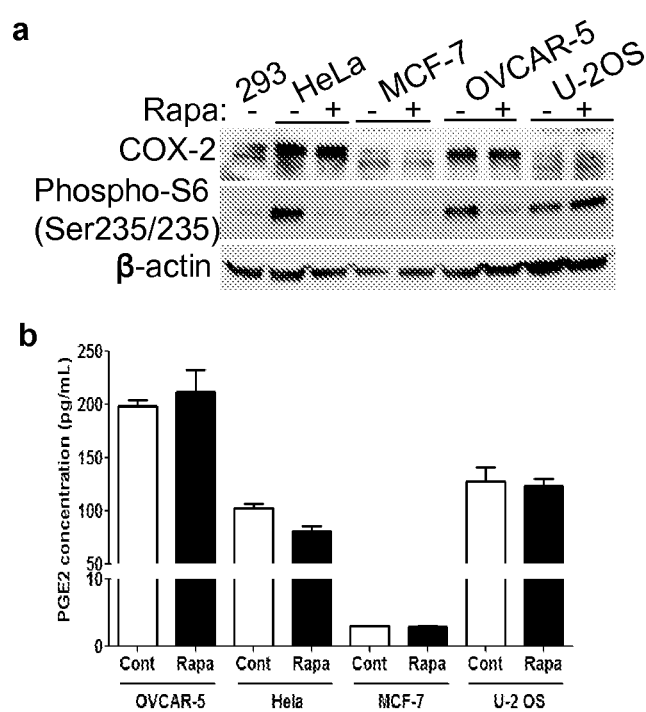

To define the molecular mechanisms responsible for estrogen-enhanced COX-2 expression and prostaglandin production, an expression array of TSC2-deficient LAM patient-derived cells (16) was analyzed (FIG. 2a) and it was found that prostacyclin synthase (PTGIS) was elevated by 40-fold and COX-2 (PTGS2) by 2-fold. Interestingly, these changes were rapamycin insensitive (FIG. 6). COX-2 protein levels were more abundant in TSC2-deficient cells compared to TSC2 reexpressing 621-101 cells (FIG. 2b). Rapamycin treatment suppressed phosphorylation of the ribosomal protein p70S6 (S6); however, did not affect COX-2 expression (data not shown), indicating that TSC2 regulates COX-2 expression in a rapamycin-insensitive manner. Levels of PGE2, 6-keto-PGF1α, PGF2α and thromboxane B2 were all significantly higher in TSC2-deficient cells relative to TSC2-reexpressing cells, and were also insensitive to rapamycin treatment (FIG. 2c). Similar results on COX-2 expression were also seen in Tsc2-deficient ELT3 cells (FIG. 2d). PGE2 levels were elevated by 2.5-fold in ELT3 cells in comparison to TSC2 reexpressing cells (FIG. 2e), and this again was not affected by rapamycin treatment (FIG. 2e). To determine whether this phenomenon of rapamycin-insensitive prostaglandin production was seen in other cells with intact TSC2 levels but mTORC1 activation, HeLa, U2OS and OVCAR5 cells were also examined. Although PGE2 production was variable among these cell lines, rapamycin did not affect COX-2 expression or PGE2 production though reducing phospho-S6 (FIG. 8). Together, these data indicate that upregulation of COX-2 and prostaglandin production is rapamycin-insensitive in cells with mTORC1 activation.

To determine whether TSC2 regulates COX-2 and prostaglandin production in vivo, xenograft tumors from mice inoculated with TSC2-deficient ELT3-V3 (vector-control) cells and TSC2-addback ELT3-T3 cells were studied. COX-2 levels were significantly higher in the ELT3-V3 xenograft tumors with elevated phospho-S6 relative to TSC2-addback ELT3-T3 tumors (FIG. 2h). In addition, urinary PGE2 and 6-keto-PGF1α levels were significantly higher in mice with the ELT3-V3 tumors in comparison to mice with the TSC2-addback ELT3-T3 tumors (FIG. 2i).

To further assess the effect of TSC2-loss on COX-2 levels in vivo, the inventors examined a spontaneously-arising renal cystadenoma from TSC2+/−mice (17), and found that COX-2 and phospho-S6 was more abundant in the TSC2-deficient tumor compared to normal kidney (FIG. 2k). Rapamycin treatment did not affect COX-2 expression in these tumors (FIG. 2l). These data indicate that COX-2 expression and prostaglandin production are enhanced in cells and tumors lacking TSC2 in a rapamycin-insensitive manner.

Aspirin Treatment Inhibits TSC2-Deficient Cell and Xenograft Tumor Growth and Reduces Urinary Levels of Prostaglandins To determine whether inhibition of COX-1 and/or COX-2 impacts the growth of LAM patient-derived cells, 621-101 cells were treated with Sulindac (a COX-1 inhibitor), NS398 (a COX-2 inhibitor), or aspirin (an irreversible COX-1 and COX-2 inhibitor) for 24 hr. NS398 and aspirin reduced COX-2 and COX-1 levels without affecting phosphorylation of MAPK or S6 (FIG. 3a). Aspirin significantly decreased PGE2 levels (FIG. 3b), and reduced proliferation of 621-101 cells (FIG. 3c). The inventors next assessed the possible benefit of aspirin in a xenograft tumor model of TSC2-deficient ELT3-luciferase-expressing cells. Aspirin treatment for two-three weeks decreased the intensity of bioluminescence (FIG. 3c), reduced the growth of xenograft tumors by 35% (FIG. 3d), and decreased the tumor size (FIG. 3e). Tumors also had reduced expression of COX-2 and c-Myc, and increased levels of cleaved-caspase-3 and cleaved-PARP (Data not shown). Furthermore, aspirin-treated mice bearing ELT3 xenograft tumors had markedly reduced urinary levels of PGE2 and 6-Keto-PGF1α (Data not shown). These data suggest that aspirin has efficacy in suppressing TSC2-deficient tumor progression.

Activation of COX-2 in LAM Nodules and Elevated Prostaglandin Production in LAM Patient Serum.

To confirm that these observations were relevant to patients with LAM, the inventors showed that LAM lungs expressed higher levels of COX-2 (PTGS2) in comparison to control lungs (FIGS. 4a and 4b). Further, COX-2 immunohistochemistry showed increased COX-2 expression in pulmonary LAM lesions (arrows), which were also positive for smooth muscle actin (SMA) and phospho-S6 (FIG. 4c). To examine the functional effect of COX-2 in LAM lungs, 15-epi-lipoxin A4 (LXA4), a product of aspirin-acetylated COX-2, was measured in exhaled breath condensate (EBC) from three LAM subjects (data not shown). 15-epi-LXA4 was detected in EBC and the levels were increased with aspirin (data not shown). Of interest, 15-epi-LXA4 decreases proliferation of A549 cells (Human lung adenocarcinoma) (18) and also suppressed the proliferation of LAM patient-derived 621-101 cells (data not shown).

Urinary PGE2 levels were measured in 29 LAM patients and in 18 healthy women; however, these levels were not significantly different between two groups (FIG. 9). Because renal prostaglandin production can significantly influence urinary prostaglandin levels, the inventors next measured PGE2 and 6-keto-PGF1α levels in sera from 14 LAM patients and 13 healthy women. Of note, the mean serum PGE2 levels of LAM patients (27.8±1.8 pg/mL) were higher than those of healthy women (19.6±1.4 pg/mL, p=0.0021) (FIG. 4d). In addition, the mean serum 6-keto-PGF1α levels of LAM patients (192.2±64.9 pg/mL) were also higher compared with levels in healthy women (82.6±6.3 pg/mL, p=0.0006) (FIG. 4e).

The inventors have found that estrogen enhances the expression of COX-2 and induces production of PGE2 and 6-keto-PGF1α in TSC2-deficient cells in vitro and in vivo. See FIG. 5. Furthermore, they identified a novel function of TSC2 as a negative regulator of COX-2 expression and prostaglandin biosynthesis. Interestingly, this regulation appears to be rapamycin-insensitive, indicating that it may be another mTORC1-independent function of TSC2. The inventors also demonstrated that COX-2 is abundant in LAM lesions, and that serum levels of PGE2 and 6-keto-PGF1α are elevated in LAM patients. Collectively, the data indicate that COX-2 plays an important role in LAM pathogenesis.

Aspirin, the prototypical non-steroidal anti-inflammatory drug, covalently modifies both COX-1 and COX-2 by acetylation. The inventors demonstrated that aspirin treatment significantly reduced the growth of xenograft tumors of TSC2-deficient ELT3 cells, and led to reduced urinary levels of PGE2 and 6-keto-PGF1α, consistent with loss of COX-1/COX-2 function. Furthermore, xenograft tumors from aspirin-treated mice exhibited higher levels of apoptosis compared to vehicle-treatment. While aspirin-acetylated COX-2 inhibits prostaglandin formation, the enzyme is not completely inactivated. Rather, aspirin-acetylated COX-2 catalyzes the conversion of arachidonate to 15-epi-LXA418. In this manner, aspirin both inhibits prostaglandin production and triggers the formation of 15-epi-LXA4, a potent inhibitor of malignant cell proliferation 18. 15-epi-LXA4 was present in EBC from LAM patients, and was increased with oral aspirin ingestion. 15-epi-LXA4 also decreased LAM-patient-derived cell proliferation. Together, these findings indicate that aspirin have rapamycin-insensitive protective actions in LAM.

LAM is often a progressive disease which leads to respiratory failure and death in the absence of lung transplantation. The recent demonstration that rapamycin has clinical benefit in LAM is a major success. However, not all patients respond to rapamycin, and upon rapamycin withdrawal, lung function decline resumes (7). Hence lifelong treatment of LAM patients with rapamycin may be required to maintain benefit, with unknown long-term toxicities. The present findings suggest that aspirin and/or other COX-1/COX-2 inhibitors may have significant benefit in slowing LAM progression and possibly other neoplastic conditions associated with mTORC1 hyperactivation. Since aspirin has a well-known side-effect profile, it is of particular clinical interest. Further clinical investigation is warranted to explore these possibilities.

REFERENCES

1. Henske, E. P. & McCormack, F. X. Lymphangioleiomyomatosis—a wolf in sheep's clothing. J Clin Invest 122, 3807-3816.
2. Krymskaya, V. P. Treatment option(s) for pulmonary lymphangioleiomyomatosis: progress and current challenges. Am J Respir Cell Mol Biol 46, 563-565.
3. McCormack, F. X., Panos, R. J. & Trapnell, B. C. (eds.). Molecular Basis of Pulmoanry Disease Insights from Rare Lung Disorders, (Human Press, New York, 2010).
4. McCormack, F. X., Travis, W. D., Colby, T. V., Henske, E. P. & Moss, J. Lymphangioleiomyomatosis: calling it what it is: a low-grade, destructive, metastasizing neoplasm. Am J Respir Crit Care Med 186, 1210-1212.
5. Taveira-Dasilva, A. M., Pacheco-Rodriguez, G. & Moss, J. The natural history of lymphangioleiomyomatosis: markers of severity, rate of progression and prognosis. Lymphat Res Biol 8, 9-19.

6. Duvel, K., et al. Activation of a metabolic gene regulatory network downstream of mTOR complex 1. Mol Cell 39, 171-183.
7. McCormack, F. X., et al. Efficacy and Safety of Sirolimus in Lymphangioleiomyomatosis. N Engl J Med.
8. Yu, J. J., et al. Estrogen promotes the survival and pulmonary metastasis of tuberin-null cells. Proc Natl Acad Sci USA 106, 2635-2640 (2009).
9. Egan, K. M., et al. COX-2-derived prostacyclin confers atheroprotection on female mice. Science 306, 1954-1957 (2004).
10. FitzGerald, G. A. & Patrono, C. The coxibs, selective inhibitors of cyclooxygenase-2. N Engl J Med 345, 433-442 (2001).
11. Wang, M. T., Honn, K. V. & Nie, D. Cyclooxygenases, prostanoids, and tumor progression. Cancer metastasis reviews 26, 525-534 (2007).
12. Muller, R. Crosstalk of oncogenic and prostanoid signaling pathways. J Cancer Res Clin Oncol 130, 429-444 (2004).
13. Wang, D. & Dubois, R. N. Eicosanoids and cancer. Nat Rev Cancer 10, 181-193.
14. Astrinidis, A., et al. Tuberin, the tuberous sclerosis complex 2 tumor suppressor gene product, regulates Rho activation, cell adhesion and migration. Oncogene 21, 8470-8476 (2002).
15. Yu, J., Astrinidis, A., Howard, S. & Henske, E. P. Estradiol and tamoxifen stimulate LAM-associated angiomyolipoma cell growth and activate both genomic and nongenomic signaling pathways. Am J Physiol Lung Cell Mol Physiol 286, L694-700 (2004).
16. Lee, P. S., et al. Rapamycin-insensitive up-regulation of MMP2 and other genes in tuberous sclerosis complex 2-deficient lymphangioleiomyomatosis-like cells. Am J Respir Cell Mol Biol 42, 227-234.
17. Onda, H., Lueck, A., Marks, P. W., Warren, H. B. & Kwiatkowski, D. J. Tsc2(+/−) mice develop tumors in multiple sites that express gelsolin and are influenced by genetic background. J Clin Invest 104, 687-695. (1999).
18. Claria, J., Lee, M. H. & Serhan, C. N. Aspirin-triggered lipoxins (15-epi-LX) are generated by the human lung adenocarcinoma cell line (A549)-neutrophil interactions and are potent inhibitors of cell proliferation. Mol Med 2, 583-596 (1996).
19. Neuman, N. A. & Henske, E. P. Non-canonical functions of the tuberous sclerosis complex-Rheb signalling axis. EMBO Mol Med 3, 189-200.
20. Yu, J. & Henske, E. P. Dysregulation of TOR Signaling in Tuberous Sclerosis and Lymphangioleiomyomatosis. in The Enzyme, Vol. 27 303-327 (Academic Press, Burlington, 2010).
21. Subbaramaiah, K., et al. Increased levels of COX-2 and prostaglandin E2 contribute to elevated aromatase expression in inflamed breast tissue of obese women. Cancer Discov 2, 356-365.
22. Howe, S. R., et al. Rodent model of reproductive tract leiomyomata. Establishment and characterization of tumor-derived cell lines. Am. J. Pathol. 146, 1568-1579. (1995).
23. Howe, S. R., Gottardis, M. M., Everitt, J. I. & Walker, C. Estrogen stimulation and tamoxifen inhibition of leiomyoma cell growth in vitro and in vivo. Endocrinology 136, 4996-5003 (1995).
24. Liu, F., et al. Real-time monitoring of tumorigenesis, dissemination, & drug response in a preclinical model of lymphangioleiomyomatosis/tuberous sclerosis complex. PLoS One 7, e38589.
25. Parkhitko, A., et al. Tumorigenesis in tuberous sclerosis complex is autophagy and p62/sequestosome 1 (SQSTM1)-dependent. Proc Natl Acad Sci USA.

What is claimed:

1. A method for treating lymphangioleiomyomatosis (LAM) in a subject in need thereof comprising administering to the subject a therapeutically effective amount of a composition comprising at least one cyclooxygenase (COX) inhibitor or an inhibitor of the prostaglandin biosynthetic pathway and at least one other compound selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil, wherein the subject is detected to have at least about 20% COX-1 and COX-2 overexpression compared with mean expression level obtained from healthy subjects.

2. The method of claim 1, wherein the subject has a mutation in the tuberous sclerosis complex (TSC) locus.

3. The method of claim 1, further comprising a step of obtaining a biological sample comprising cancer cells from the subject, wherein the cancer cells have a mutation in the TSC locus.

4. The method of claim 3, wherein the cancer cells are TSC-1 or TSC-2 deficient.

5. The method of claim 1, further comprising a step of obtaining a biological sample comprising cancer cells from the subject, wherein at least one cancer cell in the biological sample is insensitive to rapamycin.

6. The method of claim 1, further comprising a step of obtaining a biological sample comprising cancer cells from the subject, wherein at least one cancer cell in the biological sample does not involve mTOR deregulation or hyperactivity.

7. The method of claim 1, wherein the at least one other compound is selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, and A-77636.

8. The method of claim 1, wherein the subject is further treated with at least one additional therapy.

9. The method of claim 1, wherein the therapeutically effective amount of the inhibitor and/or compound is administered by a route selected from the group consisting of: aerosol, direct injection, local, systemic, intradermal, direct inhalation, intravitreal, intramuscular, intraperitoneal, intravenous, intrathecal, intrapleural, intrauterine, subcutaneous, epidural, topical, oral, transmucosal, buccal, rectal, vaginal, transdermal, intranasal, intrasynovial, intraocular/periocular, intraorgan, intratumor, and parenteral administration.

10. A method for treating lymphangioleiomyomatosis (LAM) in a subject in need thereof comprising (a) detecting the subject having a mutation in the tuberous sclerosis complex (TSC) locus and at least about 20% COX-1 and COX-2 overexpression compared with mean expression level obtained from healthy subjects; and (b) administering to the subject a therapeutically effective amount of a composition comprising at least one cyclooxygenase (COX) inhibitor or an inhibitor of the prostaglandin biosynthetic pathway and at least one other compound selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil.

11. A method for treating lymphangioleiomyomatosis (LAM) in a subject in need thereof comprising (a) detecting the subject having at least about 20% COX-1 and COX-2 overexpression compared with mean expression level obtained from healthy subjects; and (b) administering to the subject a therapeutically effective amount of a composition comprising at least one cyclooxygenase (COX) inhibitor or an inhibitor of the prostaglandin biosynthetic pathway and at least one other compound selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil.

12. A method for treating lymphangioleiomyomatosis (LAM) in a subject in need thereof comprising (a) detecting the subject having increased prostaglandin production and at least about 20% COX-1 and COX-2 overexpression compared with mean expression level obtained from healthy subjects; and (b) administering to the subject a therapeutically effective amount of a composition comprising at least one cyclooxygenase (COX) inhibitor or an inhibitor of the prostaglandin biosynthetic pathway and at least one other compound selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil.

13. A method for treating lymphangioleiomyomatosis (LAM) in a subject in need thereof comprising (a) selecting a subject who has at least one cancer cell that is insensitive to rapamycin and that has at least about 20% COX-1 and COX-2 overexpression compared with mean expression level obtained from healthy subjects; and (b) administering to the subject a therapeutically effective amount of a composition comprising at least one cyclooxygenase (COX) inhibitor or an inhibitor of the prostaglandin biosynthetic pathway and at least one other compound selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil.

14. A method for treating lymphangioleiomyomatosis (LAM) in a subject in need thereof comprising (a) selecting a subject who has at least one cancer cell that does not have mTOR deregulation or hyperactivity and that has at least about 20% COX-1 and COX-2 overexpression compared with mean expression level obtained from healthy subjects; and (b) administering to the subject a therapeutically effective amount of a composition comprising at least one cyclooxygenase (COX) inhibitor or an inhibitor of the prostaglandin biosynthetic pathway and at least one other compound selected from the group consisting of nateglinide, Z-L-Phe chloromethyl ketone, clemastine fumarate, supercinnamaldehyde, practolol, fluvastatin Na, sulindac, 6-bromoindirubin-3'-oxime, amorolfine, spectinomycin, sibutramine HCl, nelfinavir mesylate, moroxydine HCl, nicotine ditartrate, trequinsin, meglumine, tizanidine HCl, CGP-74514A hydrochloride, tioconazole, afatinib, kasugamycin, flupentixol, fluphenazine, mephenytoin, aminoglutethimide, Betaxolol hydrochloride, salmeterol, chelerythrine chloride, paroxetine, trifluoperazine, fluoxetine, methiothepin, nortriptyline, A-77636, rapamycin, SCH-202676 hydrobromide, danusertib (PHA-739358), AZ-960, nicardipine, SB-590885, Thimerosal, ionomycin, U-73343, PAF C16, BX912, and Chlorambucil.

15. The method of claim 6, wherein the sample is a blood sample.

* * * * *

UNITED STATES PATENT AND TRADEMARK OFFICE
CERTIFICATE OF CORRECTION

PATENT NO. : 9,925,202 B2
APPLICATION NO. : 14/771817
DATED : March 27, 2018
INVENTOR(S) : Jane Yu and Chenggang Li Page 1 of 1

It is certified that error appears in the above-identified patent and that said Letters Patent is hereby corrected as shown below:

In the Specification

Column 1 Lines 17-21 should read:
This invention was made with Government support under Grant No.: RO1 HL098216-3 awarded by the National Institutes of Health, and Grant No.: W8IXWH-12-1-0442 awarded by the Department of Defense. The Government has certain rights in the invention.

Signed and Sealed this
Eighteenth Day of September, 2018

Andrei Iancu
*Director of the United States Patent and Trademark Office*